United States Patent
Poznansky et al.

(10) Patent No.: US 9,229,004 B2
(45) Date of Patent: Jan. 5, 2016

(54) METHODS FOR DETECTING AND TREATING CANCER

(75) Inventors: Mark C. Poznansky, Charlestown, MA (US); Hajah Siti Fatimah Jaafar, London (GB); Dulcie V. Coleman, London (GB); Pierre Leblanc, Boston, MA (US)

(73) Assignees: THE GENERAL HOSPITAL CORPORATION, Boston, MA (US); IMPERIAL COLLEGE LONDON, London (GB)

( * ) Notice: Subject to any disclaimer, the term of this patent is extended or adjusted under 35 U.S.C. 154(b) by 135 days.

(21) Appl. No.: 13/119,663

(22) PCT Filed: Sep. 28, 2009

(86) PCT No.: PCT/US2009/058636
§ 371 (c)(1),
(2), (4) Date: Aug. 8, 2011

(87) PCT Pub. No.: WO2010/037042
PCT Pub. Date: Apr. 1, 2010

(65) Prior Publication Data
US 2011/0287949 A1 Nov. 24, 2011

Related U.S. Application Data

(60) Provisional application No. 61/100,526, filed on Sep. 26, 2008.

(51) Int. Cl.
*G01N 33/53* (2006.01)
*G01N 33/00* (2006.01)
*G01N 33/574* (2006.01)

(52) U.S. Cl.
CPC .... *G01N 33/57411* (2013.01); *G01N 33/57484* (2013.01); *G01N 2333/522* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| 7,598,028 | B2 * | 10/2009 | Macoska | 435/4 |
| 2010/0278844 | A1 | 11/2010 | Balkwill et al. | |
| 2012/0003275 | A1 * | 1/2012 | Rodrigues et al. | 424/400 |

FOREIGN PATENT DOCUMENTS

| WO | 2006/128141 A2 | 11/2006 |
| WO | 2007/112330 A2 | 10/2007 |

OTHER PUBLICATIONS

Kryczek et al. 2005. Cancer Res 65:465-472.*
Kim et al. 2008. Clin Exp Metastasis 25:201-211.*
Teicher et al. 2010. Clin. Can. Res. 16:2927-31.*
Scotton et al. 2002. Cancer Res. 62:5930-5938.*
Kodama et al. 2007. Annals of Oncology 18:70-76.*
UniProtKB P48061 1996, downloaded Jan. 30, 2013.*
FIGO guidelines 2000. International J. Gyn and Obst. 70:207-312.*
Kryczek et al. Am. J. Physiol Cell Physiol. 292:C987-C995.*
Form PCT/ISA/220, WO, filed Apr. 2, 2010, ISR for PCT/US09/58636.
Form PCT/ISA/237, WO, filed Apr. 2, 2010, Written Opinion for PCT/US09/58636.
Wei S., et al., Interleukin-2 administration alters the CD4+FOXP3+ T-cell pool and tumor trafficking in patients with ovarian carcinoma. Cancer Res. Aug. 1, 2007;67(15):7487-94.
Wald O., et al., CD4+CXCR4highCD69+ T cells accumulate in lung adenocarcinoma. J Immunol. Nov. 15, 2006;177(10):6983-90.
Shimizu Y., et al., CXCR4+FOXP3+CD25+ lymphocytes accumulate in CXCL 12-expressing malignant CXCR4+FOXP3+CD25+ pleural mesothelioma. Int J Immunopathol Pharmacol. Jan.-Mar. 2009;22(1):43-51.
Majka M., et al., SDF-1 alone and in co-operation with HGF regulates biology of human cervical carcinoma cells. Folia Histochem Cytobiol. 2006;44(3):155-64.
Balkwill, Nature, 4:540-550 (2004). "Cancer and the Chemokine Network."
Beyer et al., Blood, 108(3):804-811 (2006). "Regulatory T cells in cancer."
Brand et al., Experimental Cell Research, 310:117-130 (2005). "CXCR4 and CSCL12 are inversely expressed in colorectal cancer cells and modulate cancer cell migration, invasion and MMP-9 activation."
Hassan et al., The American Journal of Pathology, 175(1):66-73 (2009). "The Influence of Tumor-Host Interactions in the Stromal Cell-Derived Factor-1/CXCR4 Ligand/Receptor Axis in Determining Metastatic Risk in Breast Cancer."
Jaffar et al., The American Journal of Pathology, 175(4):1525-1535 (2009). "Correlation of CXCL12 Expression and FoxP3+ Cell Infiltration with Human Papillomavirus Infection and Clinicopathological Progression of Cervical Cancer."
Kang et al., Breast Cancer Research, 7:R402-R410 (2005). "Stromal cell derived factor-1: its influence on invasiveness and migration of breast cancer cells in vitro, and its association with prognosis and survival in human breast cancer."
Kodama et al., Annals of Oncology, 18:70-76 (2007). "Association of CXCR4 and CCR7 chemokine receptor expression and lymph node metastasis in human cervical cancer."
Kryczek et al., Cancer Immunol Immunother, 51:513-519 (2002). "Accumulation of CD45RO+ cells in peritoneal carcinomatous fluid favours survival of ovarian carcinoma patients."
Scotton et al., Cancer Research, 62:5930-5938 (2002). "Multiple Actions of the Chemokine CXCL12 on Epithelial Tumor Cells in Human Ovarian Cancer."

(Continued)

*Primary Examiner* — Shulamith H Shafer
(74) *Attorney, Agent, or Firm* — Nixon Peabody LLP

(57) ABSTRACT

The invention generally features compositions and methods for the diagnosis, treatment, and monitoring of neoplasia in a subject, as well as methods of treatment selection.

7 Claims, 11 Drawing Sheets

(56) References Cited

OTHER PUBLICATIONS

UNIPROTKB. Stromal cell derived factor 1.1 Feb. 1996 [Retrieved from the internet on Feb. 3, 2010:<URL: http://www.uniprot.org/uniprot/P48061>); p. 4-5.

Yu et al., Gene, 374:174-179 (2006). "Identification and expression of novel isoforms of human stromal cell-derived factor 1."

Zhang et al., Int J Gynecol Cancer, 17:478-483 (2007). "Study on CXCR4/SDF-1alpha axis in lymph node metastasis of cervical squamous cell carcinoma."

Zitvogel et al., The Journal of Clinical Investigation, 118(6):1991-2001 (2008). "The anticancer immune response: indispensable for therapeutic success?".

* cited by examiner

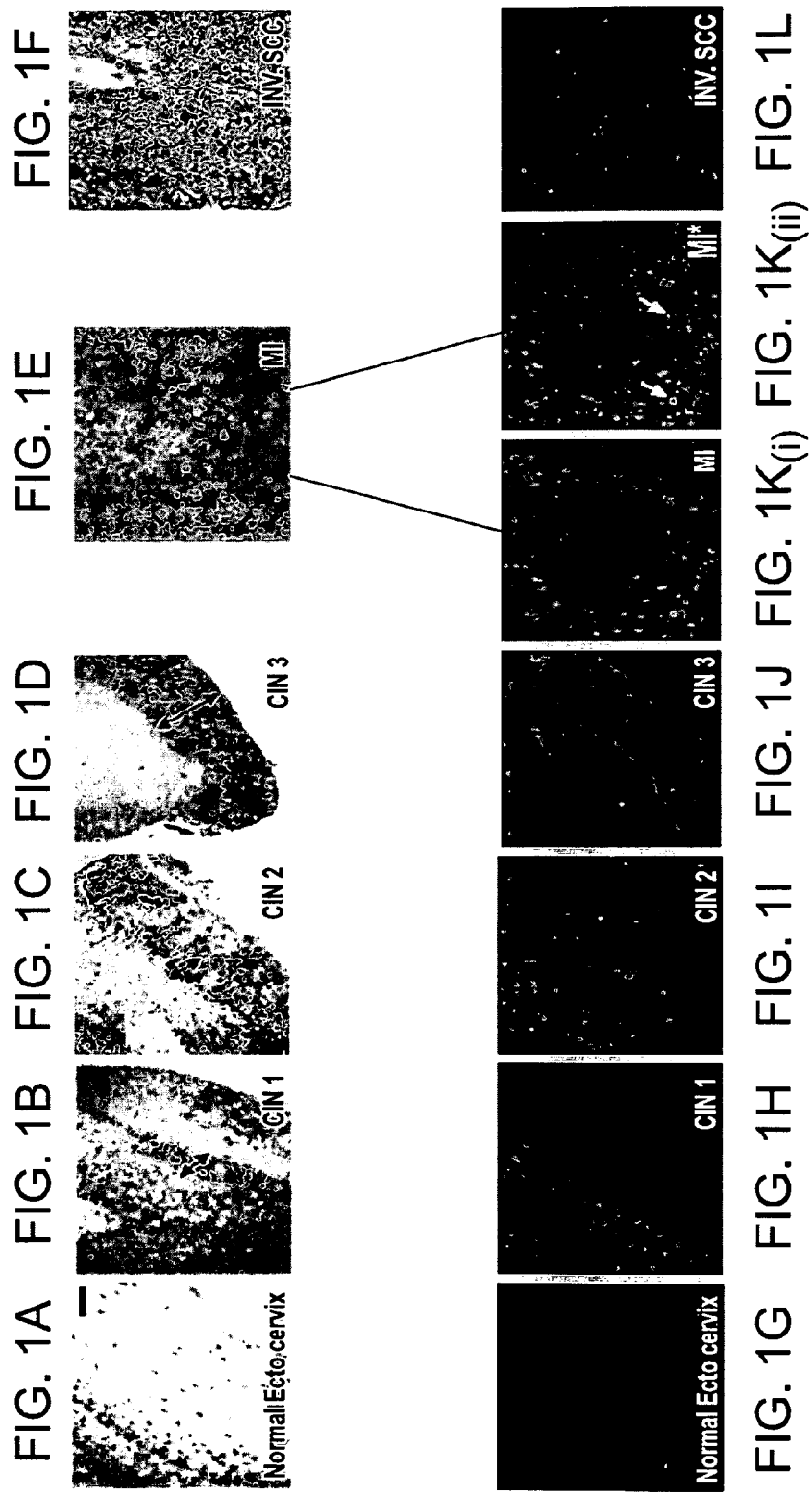

FIG. 1M  FIG. 1N  FIG. 1O
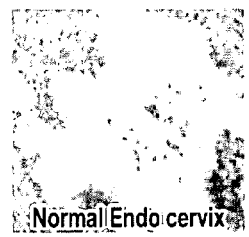 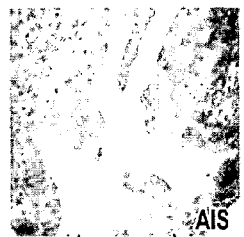 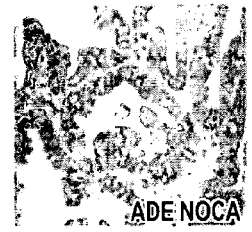
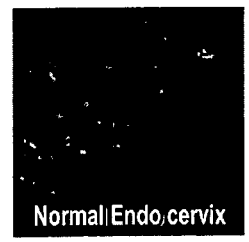 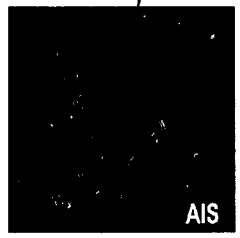  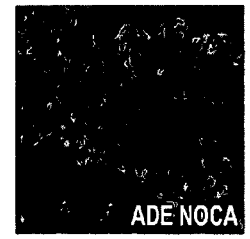
FIG. 1P  FIG. 1Q(i)  FIG. 1Q(ii)  FIG. 1R

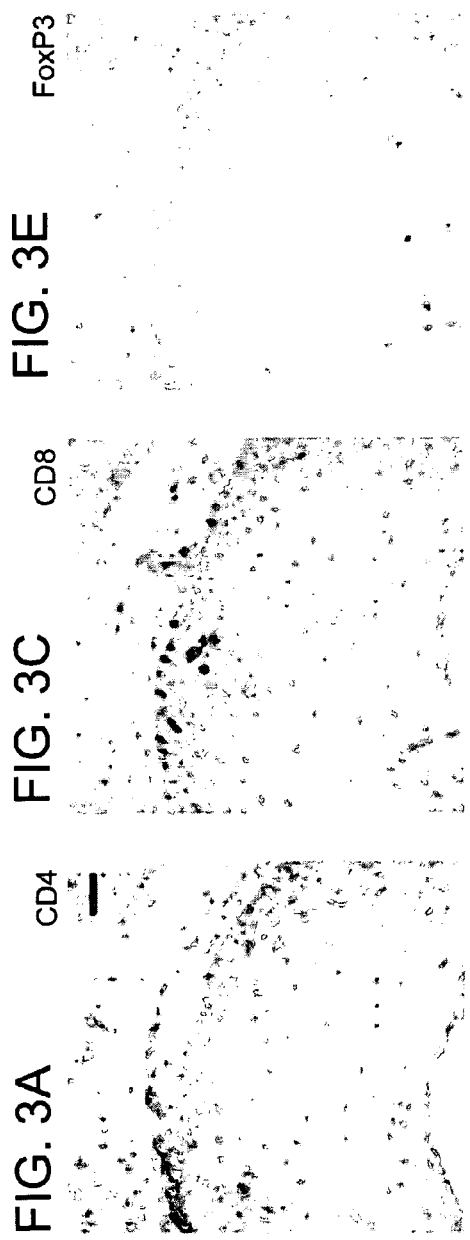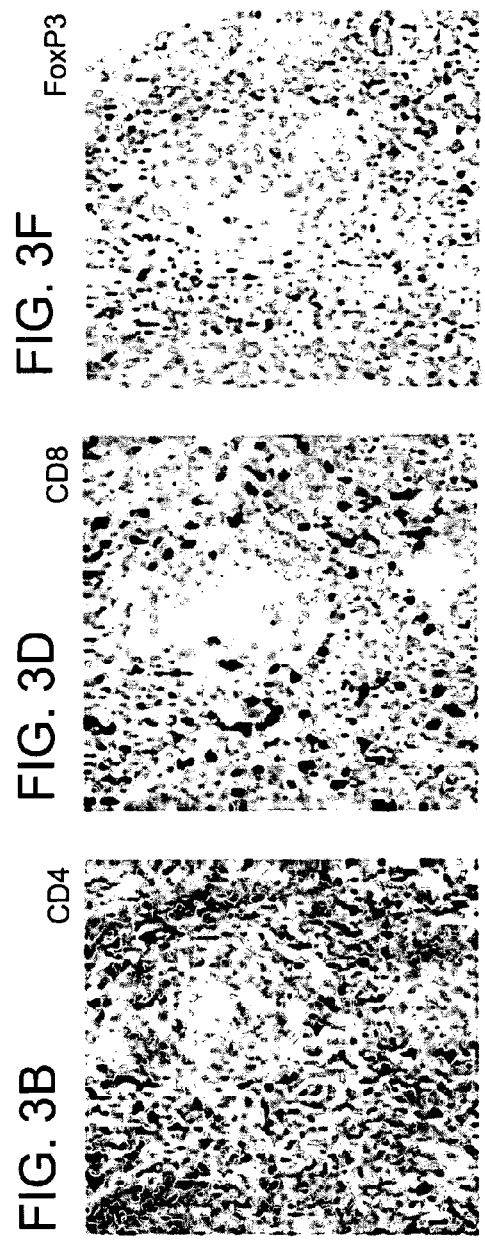

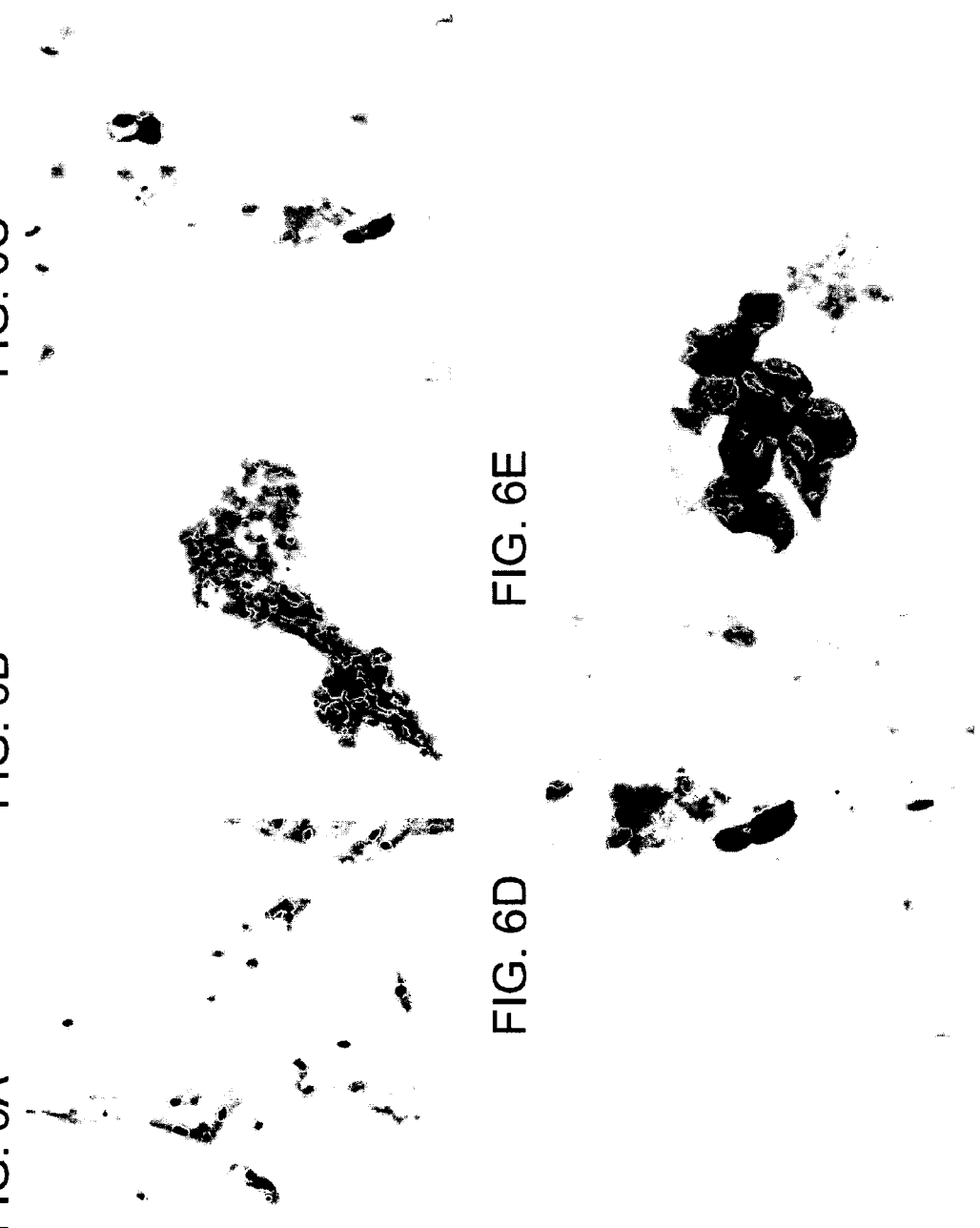

- 1 Exp5 tumor S1, 5/12/08 (BR5)
- 2 Exp6 tumor, S1, 6/30/08 (BR5)
- 3 1D8 N5, tumor, 9/17/08
- 4 AMD treated BR5, tumor, 5/28/08

SEQUENCE LISTING

```
<160> NUMBER OF SEQ ID NOS: 7

<210> SEQ ID NO 1
<211> LENGTH: 396
<212> TYPE: PRT
<213> ORGANISM: Homo sapiens

<400> SEQUENCE: 1

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Ser Leu Asn Pro Met
    50                  55                  60

Pro Pro Ser Gln Leu Gln Leu Ser Thr Val Asp Ala His Ala Arg Thr
65                  70                  75                  80

Pro Val Leu Gln Val His Pro Leu Glu Ser Pro Ala Met Ile Ser Leu
                85                  90                  95

Thr Pro Pro Thr Thr Ala Thr Gly Val Phe Ser Leu Lys Ala Arg Pro
            100                 105                 110

Gly Leu Pro Pro Gly Ile Asn Val Ala Ser Leu Glu Trp Val Ser Arg
        115                 120                 125

Glu Pro Ala Leu Leu Cys Thr Phe Pro Asn Pro Ser Ala Pro Arg Lys
    130                 135                 140

Asp Ser Thr Leu Ser Ala Val Pro Gln Ser Ser Tyr Pro Leu Leu Ala
145                 150                 155                 160

Asn Gly Val Cys Lys Trp Pro Gly Cys Glu Lys Val Phe Glu Glu Pro
                165                 170                 175

Glu Asp Phe Leu Lys His Cys Gln Ala Asp His Leu Leu Asp Glu Lys
            180                 185                 190

Gly Arg Ala Gln Cys Leu Leu Gln Arg Glu Met Val Gln Ser Leu Glu
        195                 200                 205

Gln Gln Leu Val Leu Glu Lys Glu Lys Leu Ser Ala Met Gln Ala His
    210                 215                 220

Leu Ala Gly Lys Met Ala Leu Thr Lys Ala Ser Ser Val Ala Ser Ser
225                 230                 235                 240

Asp Lys Gly Ser Cys Cys Ile Val Ala Ala Gly Ser Gln Gly Pro Val
```

```
                         245                 250                 255
Val Pro Ala Trp Ser Gly Pro Arg Glu Ala Pro Asp Ser Leu Phe Ala
            260                 265                 270

Val Arg Arg His Leu Trp Gly Ser His Gly Asn Ser Thr Phe Pro Glu
    275                 280                 285

Phe Leu His Asn Met Asp Tyr Phe Lys Phe His Asn Met Arg Pro Pro
290                 295                 300

Phe Thr Tyr Ala Thr Leu Ile Arg Trp Ala Ile Leu Glu Ala Pro Glu
305                 310                 315                 320

Lys Gln Arg Thr Leu Asn Glu Ile Tyr His Trp Phe Thr Arg Met Phe
                325                 330                 335

Ala Phe Phe Arg Asn His Pro Ala Thr Trp Lys Asn Ala Ile Arg His
            340                 345                 350

Asn Leu Ser Leu His Lys Cys Phe Val Arg Val Glu Ser Glu Lys Gly
        355                 360                 365

Ala Val Trp Thr Val Asp Glu Leu Glu Phe Arg Lys Lys Arg Ser Gln
    370                 375                 380

Arg Pro Ser Arg Cys Ser Asn Pro Thr Pro Gly Pro
385                 390                 395

<210> SEQ ID NO 2
<211> LENGTH: 89
<212> TYPE: PRT
<213> ORGANISM: Homo sapiens

<400> SEQUENCE: 2

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys
                85

<210> SEQ ID NO 3
<211> LENGTH: 93
<212> TYPE: PRT
<213> ORGANISM: Homo sapiens

<400> SEQUENCE: 3

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
```

<210> SEQ ID NO 4
<211> LENGTH: 119
<212> TYPE: PRT
<213> ORGANISM: Homo sapiens

<400> SEQUENCE: 4

```
Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
                35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Gly Arg Arg Glu Glu Lys Val
                85                  90                  95

Gly Lys Lys Glu Lys Ile Gly Lys Lys Arg Gln Lys Lys Arg Lys
                100                 105                 110

Ala Ala Gln Lys Arg Lys Asn
        115
```

<210> SEQ ID NO 5
<211> LENGTH: 140
<212> TYPE: PRT
<213> ORGANISM: Homo sapiens

<400> SEQUENCE: 5

```
Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
                35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Asn Leu Ile Ser Ala Ala Pro Ala
                85                  90                  95

Gly Lys Arg Val Ile Ala Gly Ala Arg Ala Leu His Pro Ser Pro Pro
                100                 105                 110

Arg Ala Cys Pro Thr Ala Arg Ala Leu Cys Glu Ile Arg Leu Trp Pro
        115                 120                 125

Pro Pro Glu Trp Ser Trp Pro Ser Pro Gly Asp Val
        130                 135                 140
```

<210> SEQ ID NO 6
<211> LENGTH: 90
<212> TYPE: PRT
<213> ORGANISM: Homo sapiens

<400> SEQUENCE: 6

```
Met Asn Ala Lys Val Val Val Leu Val Leu Val Leu Thr Ala Leu
1               5                   10                  15
```

```
Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Cys
                85                  90

<210> SEQ ID NO 7
<211> LENGTH: 100
<212> TYPE: PRT
<213> ORGANISM: Homo sapiens

<400> SEQUENCE: 7

Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Ile Trp Leu Tyr Gly Asn Ala
                85                  90                  95

Glu Thr Ser Arg
            100
```

METHODS FOR DETECTING AND TREATING CANCER

STATEMENT OF RIGHTS TO INVENTIONS MADE UNDER FEDERALLY SPONSORED RESEARCH

This work was supported by the following grants from the National Institutes of Health, Grant Nos: RO1 AI49757. The government has certain rights in the invention.

CROSS-REFERENCE TO RELATED APPLICATION

This application is the U.S. national phase, pursuant to 35 U.S.C. §371, of PCT international application Ser. No. PCT/US2009/058636, filed Sep. 28, 2009, designating the United States and published in English on Apr. 1, 2010 as publication WO 2010/037042 A2, which claims priority to U.S. Provisional Application Ser. No. 61/100,526, filed on Sep. 26, 2008. The entire contents of the aforementioned patent applications are incorporated herein by this reference.

SEQUENCE LISTING

The instant application contains a Sequence Listing which has been submitted in ASCII format via EFS-Web and is hereby incorporated by reference in its entirety. Said ASCII copy, created on Nov. 6, 2009, is named 69968WO5 and is 9,482 bytes in size.

BACKGROUND OF THE INVENTION

Although great strides have been made in detecting and treating a variety of neoplasias, cancer rates and cancer mortality rates remain unacceptably high. There are a number of cancers that are of particular concern to women, including breast, ovarian, and cervical cancer. 10 percent of women will develop breast cancer and almost 2 percent will develop ovarian cancer during their life times. Moreover, cervical cancer is second only to breast cancer as a cause of death in women. Preinvasive and early invasive stages are recognized for all the above mentioned cancer and it is well established that Early detection can significantly improve long-term survival. This has been amply demonstrated by the relative success of the cervical cancer and breast cancer screening programs, which aim to detect cervical cancer/breast cancer at the preinvasive stage. Early cancers usually show no symptoms or signs and must often be detected by screening or diagnosis. Typically symptoms of late cervical cancer develop after lesions invade nearby tissue. Curative and preventative treatment (e.g., surveillance, minor surgery, and hormone therapy) is feasible for patients with detection of preinvasive or early invasive cancers (e.g., cervical intraepithelial neoplasia (CIN) is the preinvasive stage of squamous cervical cancer). Whereas treatment is much more aggressive and debilitating in advanced cancers. A need exists for more sensitive, automatable and specific tests for the detection of preinvasive and invasive carcinoma, including breast, ovary, cervix) and for methods of determining the invasive or malignant potential of the preinvasive neoplastic lesions.

SUMMARY OF THE INVENTION

As described below, the present invention features compositions and methods for diagnosing, monitoring or selecting a therapy for a neoplasia (e.g., ovarian, cervical, melanoma, and renal carcinomas), as well as compositions and methods for treating the neoplasia. As reported in more detail below, the invention presented here has been proven to be effective in detecting and discriminating between preinvasive and invasive cervical carcinomas and is useful for the diagnosis, screening and treatment of this cancer. Based on these results, it is similarly effective in a wide range of other cancers, particularly those which have preinvasive, early and late invasive stage In one aspect, the invention generally features a method for identifying a neoplasia in a biologic sample, the method involving detecting the presence of a CXCL12 polypeptide that has a molecular weight greater than about 10, 11, 12, 13, 14, or 15 kD, where the presence of the CXCL12 polypeptide identifies the presence of a neoplasia in the sample.

In another aspect, the invention generally features a method for identifying the presence or absence of a neoplasia in a biologic sample, the method involving detecting an increase in the level of a CXCL12 polypeptide having a molecular weight greater than about 10 kD in a sample relative to a reference, where detection of an increase identifies the presence of a neoplasia.

In yet another aspect, the invention features a method of determining the clinical aggressiveness or stage of a neoplasia in a biologic sample, the method involving detecting the level of a CXCL12 polypeptide having a molecular weight greater than about 10, 11, 12, 13, 14, or 15 kD in the sample, where an increased level of CXCL12 relative to a reference indicates an increased clinical aggressiveness or stage of the neoplasia.

In yet another aspect, the invention features a method for monitoring a neoplasia in a subject, the method involving detecting an alteration in the level of a CXCL12 polypeptide that has a molecular weight greater than about 10, 11, 12, 13, 14, or 15 kD, where an increase in the level of the CXCL12 polypeptide relative to a reference level previously obtained from the subject identifies progression of the neoplasia in the subject, and reduction of the level of the CXCL12 polypeptide relative to the references identifies failure of the neoplasia to progress in the subject.

In yet another aspect, the invention features a method for identifying the presence or absence of a cervical neoplasia in a biologic sample, the method involving detecting the level of CXCL12, forkhead box P3 (FoxP3), or a combination thereof in the sample relative to a reference, where an increase in the level identifies a cervical neoplasia.

In still another aspect, the invention features a method of determining the clinical aggressiveness of a cervical neoplasia in a biologic sample, the method involving detecting the level of CXCL12, FoxP3, or a combination thereof in the sample, where an increased level of CXCL12, FoxP3, or a combination thereof relative to a reference indicates an increased clinical aggressiveness of the cervical neoplasia.

In still another aspect, the invention features a method of determining the stage of a cervical neoplasia in a biologic sample, the method involving quantifying the level of CXCL12, FoxP3, or a combination thereof in the sample, where an increased level of CXCL12, FoxP3, or a combination thereof in the sample relative to a reference indicates an increased stage of the cervical neoplasia.

In another aspect, the invention generally features a method for detecting or staging cervical carcinoma in a subject, the method involving detecting the presence or absence of CXCL12 polypeptide in a cervical cell or tissue sample using an immunoassay relative to a reference; and detecting the number of FoxP3-expressing T cells in the sample in an immunoassay relative to a reference, where an increase in the level of CXCL12 and an increase in the number of FoxP3, or a combination thereof relative to a control detects a cervical neoplasia and the absence of an increase detects the absence of a cervical neoplasia in the biologic sample.

In another aspect, the invention generally features a method for identifying a subject as having or having a propensity to develop a cervical neoplasia, the method involving detecting an increase in CXCL12, FoxP3, or a combination thereof in a subject sample, thereby identifying the subject as having or having a propensity to develop CIN or invasive cervical carcinoma. In one embodiment, the sample is obtained in a cone biopsy, culposcopy, or by scraping or abrading the cervical epithelium.

In another aspect, the invention generally features a method of determining the clinical aggressiveness of a cervical cancer in a subject, the method involving quantifying the level of CXCL12, FoxP3, or a combination thereof in the sample, where an increased level of CXCL12, FoxP3, or a combination thereof relative to a reference indicates an increased clinical aggressiveness of cervical cancer.

In another aspect, the invention generally features a method of determining the prognosis of a subject diagnosed as having cervical neoplasia, the method involving quantifying the level of CXCL12, FoxP3, or a combination thereof in a sample derived from the subject, where an altered level of CXCL12, FoxP3, or a combination thereof relative to a reference indicates the prognosis of the subject.

In another aspect, the invention generally features a method of selecting an appropriate treatment regimen for a subject identified as having cervical neoplasia, the method involving quantifying the level of CXCL12, FoxP3, or a combination thereof in a biologic sample from the subject relative to a reference, where the level of CXCL12, FoxP3, or a combination thereof is indicative of a treatment; and selecting an appropriate treatment, where a minimal increase in the level of CXCL12, FoxP3, or a combination thereof indicates that a less aggressive treatment is appropriate, and a significant increase in the level of CXCL12 indicates that a more aggressive treatment regimen is appropriate.

In another aspect, the invention generally features a method of monitoring a subject diagnosed as having cervical neoplasia, the method involving quantifying the level of CXCL12, FoxP3, or a combination thereof in a sample derived from the subject, where an altered level of CXCL12, FoxP3, or a combination thereof relative to the level of CXCL12, FoxP3, or a combination thereof in a reference indicates an altered severity of cervical neoplasia in the subject. In one embodiment, the reference is the level of CXCL12, FoxP3, or a combination thereof present in a sample previously obtained from the subject. In another embodiment, the reference is a baseline level of CXCL12, FoxP3, or a combination thereof present in a sample from the subject obtained prior to therapy. In yet another embodiment, where the reference is the level of CXCL12, FoxP3, or a combination thereof present in a normal patient sample. In another aspect, the invention generally features a kit for the analysis of the level of CXCL12, FoxP3, or a combination thereof, the kit comprising at least one reagent capable of detecting CXCL12 protein or polynucleotide, FoxP3 protein or polynucleotide, or a combination thereof and directions for using the reagent for the analysis of the level of CXCL12, FoxP3, or a combination thereof. In one embodiment, the reagent is an anti-CXCL12 antibody, anti-FoxP3, antibody, or fragment thereof. In another embodiment, the reagent is a detectable probe capable of binding an CXCL12 or FoxP3 polypeptide or polynucleotide. In yet another embodiment, the probe is detected by fluorescence, by autoradiography, by an immunoassay, by an enzymatic assay, chemiluminescence, or by a colorimetric assay.

In another aspect, the invention generally features a method of treating or preventing neoplasia in a subject in need thereof by administering to the subject an effective amount of an agent that reduces the expression or activity of FoxP3 or a CXCL12 polypeptide having a molecular weight greater than about 10 kd relative to a reference, thereby treating the subject. In one embodiment, the neoplasia is selected from the group consisting of ovarian, breast, cervical, melanoma, and renal carcinomas. In another embodiment, the agent is an inhibitory nucleic acid molecule (e.g., an antisense molecule, an siRNA, and an shRNA) that is complementary to at least a portion of a FoxP3 nucleic acid molecule or a nucleic acid molecule encoding a CXCL12 polypeptide having a molecular weight greater than about 10 kd relative to a reference. In yet another embodiment, the agent is a small compound (e.g., AMD3100) or an antibody or fragment thereof that selectively binds to FoxP3 or a CXCL12 polypeptide having a molecular weight greater than about 10 kd relative to a reference. In another embodiment, the antibody is a monoclonal or polyclonal antibody. In yet another embodiment, the agent is topically applied. In yet another embodiment, the method comprises administering the agent by mucosal delivery. In yet another embodiment, the neoplasia is reduced in size relative to the size of the neoplasia prior to treatment.

In another aspect, the invention generally features a CXCL12 polypeptide having a molecular weight greater than about 10, 11, 12, 13, 14, or 15 kd, where the polypeptide binds an anti-CXCL12 antibody, and has chemokine or fugetaxis activity. In one embodiment, the polypeptide comprises at least 30-100 amino acids having at least 85% identity to a CXCL12 gamma or delta isoform polypeptide. In another embodiment, the polypeptide comprises at least a portion of the amino acid sequence of a CXCL12 gamma or delta isoform polypeptide.

In another aspect, the invention generally features a CXCL12 nucleic acid molecule encoding the CXCL12 polypeptide.

In another aspect, the invention generally features an inhibitory nucleic acid molecule that is complementary to at least a fragment of the CXCL12 nucleic acid molecule.

In another aspect, the invention generally features a pharmaceutical composition containing an inhibitory nucleic acid molecule that is complementary to at least a portion of a FoxP3 nucleic acid molecule or a nucleic acid molecule encoding a CXCL12 polypeptide having a molecular weight greater than about 10, 11, 12, 13, 14, or 15 kd for use in treating neoplasia.

In another aspect, the invention generally features a pharmaceutical composition containing an antibody that specifically binds a FoxP3 polypeptide or a CXCL12 polypeptide having a molecular weight greater than about 10 kd for use in treating neoplasia.

In various embodiments of the above aspects or of any aspect of the invention delineated herein, a CXCL12 polypeptide is one having a molecular weight greater than about 10-11 kD (e.g., greater than about 10, 10.1, 10.2, 10.3, 10.4, 10.5, 10.6, 10.7, 10.8, 10.9, 11, 11.1, 11.2). In various embodiments, a CXCL12 molecular weight is determined in an immunoassay, in an SDS-PAGE assay, by mass spectroscopy, by Western blot, by ELISA, or by any other means known in the art. In another embodiment of the above aspects, the CXCL12 polypeptide binds a CXCL12-specific antibody. In still other embodiments of the above aspects, the CXCL12 polypeptide has at least about 85%, 90%, 95%, 96%, 97%, 98%, 99%, or 100% identity to the amino acid sequence of CXCL12 isoform listed in Table 1. In still another embodiment of the above aspects, the CXCL12 polypeptide is less than 100% identical to the sequence of a CXCL12 sequence provided at Table 1. In another embodiment of the above aspects, the CXCL12 polypeptide has chemotaxis or fugetaxis activity. In still another embodiment of the above aspects, the absence of an increase when compared to normal control tissue identifies the absence of a neoplasia in the biologic sample. In still other embodiments of the above aspects, the level of CXCL12 and of FoxP3 is quantified. In still other embodiments of the above aspects, levels of FoxP3 are detected by detecting FoxP3-expressing T cells. In still other embodiments of the above aspects, the method further involves detecting CD3-expressing T cells. In still another embodiment of the above aspects, the biologic sample is a patient sample. In still other embodiments of the above aspects or any other aspect of the invention delineated herein, the method further involves characterizing HPV status of the patient. In still another embodiment of the above aspects, the sample is a tissue sample, cellular sample (e.g., a sample obtained by a surgical procedure, by colposcopy, or by scraping or abrading the cervical epithelium) or a biologic fluid. In still other embodiments of the above aspects, the reference is the level of CXCL12, FoxP3, or combination thereof present in a control sample (e.g., a healthy control subject or a sample obtained from the subject prior to treatment). In still another embodiment of the above aspects, the level of FoxP3 is measured by counting the number of FoxP3-expressing T cells in a neoplastic lesion or tumor relative to the number present in a normal control tissue. In still another embodiment of the above aspects, the level of CXCL12, FoxP3, or a combination thereof is quantified by an immunoassay, immunohistochemical staining, or a combination thereof. In still another embodiment of the above aspects, CXCL12, FoxP3, or a combination thereof is measured by Western blotting, ELISA, FACS, lateral flow device, or protein microarray. In still another embodiment of the above aspects, the method further involves communicating the results to a human patient. For example, the results are communicated in a readable form (e.g., a computer readable form, paper copy, or other form). In still other embodiments of the above aspects, the level of CXCL12, FoxP3, or a combination thereof is measured using a hybridization probe, microarray, Northern blot, PCR, quantitative reverse transcriptase PCR, or a combination thereof. In still another embodiment of the above aspects, CXCL12, FoxP3, or a combination thereof is increased by at least about 2-, 3-, 4-, 5-, 10-, or 20-fold relative to a reference. In still another embodiment of the above aspects, a minimal increase of less than about 2-fold or less in the level of CXCL12, FoxP3, or a combination thereof relative to a reference indicates that a less aggressive treatment regimen is appropriate. In still another embodiment of the above aspects, the less aggressive treatment regimen is selected from the group consisting of cancer surveillance, loop electrical excision procedure (LEEP), trachelectomy, and hormonal therapy. In still another embodiment of the above aspects, an increase of about 5-fold, 10-fold, 15-fold, 20-fold or more in the level of CXCL12, FoxP3, or a combination thereof relative to a reference indicates that a more aggressive treatment regimen is appropriate. In still another embodiment of the above aspects, the more aggressive treatment regimen is selected from the group consisting of hysterectomy, radiation therapy, and chemotherapy. In still another embodiment of the above aspects or any other aspect delineated herein, the subject is a human patient. In various embodiments, the reference is the level of CXCL12, FoxP3, or a combination thereof present in a sample previously obtained from the subject. In another embodiment, the reference is a baseline level of CXCL12, FoxP3, or a combination thereof present in a sample from the subject obtained prior to therapy. In yet another embodiment, where the reference is the level of CXCL12, FoxP3, or a combination thereof present in a normal patient sample. In still other embodiments of the above aspects, the inhibitory nucleic acid molecule is selected from the group consisting of an antisense molecule, an siRNA, and an shRNA. In still other embodiments of the above aspects, the composition is topically applied. In still other embodiments of the above aspects, the composition is administered by mucosal delivery.

The invention provides compositions and methods for the detection of neoplasia or a propensity to develop a neoplasia. Other features and advantages of the invention will be apparent from the detailed description, and from the claims.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "alteration" is meant an increase or decrease. An alteration may be by as little as 1%, 2%, 3%, 4%, 5%, 10%, 20%, 30%, or by 40%, 50%, 60%, or even by as much as 75%, 80%, 90%, or 100%.

By "selectively binds" is meant that an agent binds a CXCL12 or FoxP3 polypeptide or nucleic acid molecule present in a sample, but does not substantially bind to other components present in the sample. In one embodiment, an agent selectively binds a sequence found in a CXCL12 polypeptide having a molecular weight greater than about 10 kD or 11 kD, but does not bind to CXCL12 polypeptides having a molecular weight less than about 10 kD or 11 kD.

By "biologic sample" is meant any tissue, cell, fluid, or other material derived from an organism.

By "clinical aggressiveness" is meant the severity of a neoplasia. Aggressive neoplasias are more likely to metastasize than less aggressive neoplasias. While conservative methods of treatment are appropriate for less aggressive neoplasias, more aggressive neoplasias require more aggressive therapeutic regimens.

By "control" or "reference" is meant a standard of comparison. For example, the level of CXCL12 or FoxP3 in a neoplasia may be compared to the level of CXCL12 or FoxP3, respectively, in a corresponding normal or healthy tissue.

By "diagnostic" is meant any method that identifies the presence of a pathologic condition or characterizes the nature of a pathologic condition (e.g., cervical neoplasia). Diagnostic methods differ in their sensitivity and specificity. While a particular diagnostic method may not provide a definitive diagnosis of a condition, it suffices if the method provides a positive indication that aids in diagnosis.

By "FoxP3 polypeptide" is meant a protein or fragment thereof having at least 85% amino acid sequence identity to NP 001107849 or a fragment thereof and having transcriptional regulatory or immunoregulatory function. The sequence of an exemplary FoxP3 polypeptide is provided below (SEQ ID NO: 1).

```
  1 mpnprpgkps apslalgpsp gaspswraap kasdllgarg pggtfqgrdl
    rggahassss 61 lnpmppsqlq lstvdahart pvlqvhples pamisltppt tatgvfslka
    rpglppginv 121 aslewvsrep allctfpnps aprkdstlsa vpqssyplla ngvckwpgce
    kvfeepedfl 181 khcqadhlld ekgraqcllq remvqsleqq lvlekeklsa mqahlagkma
    ltkassvass 241 dkgsccivaa gsqgpvvpaw sgpreapdsl favrrhlwgs hgnstfpefl
    hnmdyfkfhn 301 mrppftyatl irwaileape kqrtlneiyh wftrmfaffr nhpatwknai
    rhnlslhkcf 361 vrvesekgav wtvdelefrk krsqrpsrcs nptpgp
```

By "FoxP3 polynucleotide" is meant a nucleic acid molecule encoding a FoxP3 polypeptide.

By "FoxP3 biological activity" is meant transcriptional regulatory or immunoregulatory activity.

By "inhibitory nucleic acid molecule" is meant a polynucleotide that disrupts the expression of a target nucleic acid molecule or an encoded polypeptide. Exemplary inhibitory nucleic acid moelcules include, but are not limited to, shRNAs, siRNAs, antisense nucleic acid molecules, and analogs thereof.

By "CXCL12 or SDF-1 polypeptide" is meant a protein or fragment thereof that binds a CXCL12 specific antibody and that has chemotaxis or fugetaxis activity. Chemotaxis or fugetaxis activity is determined by assaying the direction of T cell migration (e.g., toward or away from an agent of interest). See, for example, Poznansky et al., Nature Medicine 2000, 6:543-8. In one embodiment, the CXCL12 polypeptide has a molecular weight greater than about 8, 8.5, 9, 10, 10.5, 11, 11.5, 12, 12.5, 13, 13.5, 14, 14.5, 15, 15.5, or 16 kD. Note that the terms CXCL12 and SDF-1 may be used interchangeably. In one embodiment, a CXCL12 polypeptide has at least about 85%, 90%, 95%, or 100% amino acid sequence identity to NP_001029058 and has chemokine or fugetaxis activity. Exemplary SDF1 Isoforms are provided in Table 1 (below).

TABLE 1

HUMAN SDF1 ISOFORMS

| Name | Accession Number | Accession Number versions | Sequence | Mwt | SEQ ID NO: |
|---|---|---|---|---|---|
| SDF-1 Alpha | NP_954637 | NP_954637.1 GI: 40316924 | MNAKVVVVLV LVLTALCLSD GKPVSLSYRC PCRFFESHVA RANVKHLKIL NTPNCALQIV ARLKNNNRQV CIDPKLKWIQ EYLEKALNK | 10102.6 | 2 |
| SDF-1 Beta | P48061 | P48061.1 GI: 1352728 | MNAKVVVVLV LVLTALCLSD GKPVSLSYRC PCRFFESHVA RANVKHLKIL NTPNCALQIV ARLKNNNRQV CIDPKLKWIQ EYLEKALNKR FKM | 10665.31 | 3 |
| SDF-1 Gamma | NP_001029058 | NP_001029058.1 GI: 76563933 | MNAKVVVVLV LVLTALCLSD GKPVSLSYRC PCRFFESHVA RANVKHLKIL NTPNCALQIV ARLKNNNRQV CIDPKLKWIQ EYLEKALNKG RREEKVGKKE KIGKKKRQKK RKAAQKRKN | 13704.81 | 4 |
| SDF-1 Delta | | Yu et al. Identification and expression of novel isoforms of human stromal cell-derived factor 1. Gene (2006) vol. 374 pp. 174-9 | MNAKVVVVLV LVLTALCLSD GKPVSLSYRC PCRFFESHVA RANVKHLKIL NTPNCALQIV ARLKNNNRQV CIDPKLKWIQ EYLEKALNNL ISAAPAGKRV IAGARALHPS PPRACPTARA LCEIRLWPPP EWSWPSPGDV | 15494.59 | 5 |

TABLE 1-continued

HUMAN SDF1 ISOFORMS

| Name | Accession Number | Accession Number versions | Sequence | Mwt | SEQ ID NO: |
|---|---|---|---|---|---|
| SDF-1 Epsilon | | Yu et al. Identification and expression of novel isoforms of human stromal cell-derived factor 1. Gene (2006) vol. 374 pp. 174-9 | MNAKVVVVLV LVLTALCLSD GKPVSLSYRC PCRFFESHVA RANVKHLKIL NTPNCALQIV ARLKNNNRQV CIDPKLKWIQ EYLEKALNNC | 10191.67 | 6 |
| SDF-1 Phi | | Yu et al. Identification and expression of novel isoforms of human stromal cell-derived factor 1. Gene (2006) vol. 374 pp. 174-9 | MNAKVVVVLV LVLTALCLSD GKPVSLSYRC PCRFFESHVA RANVKHLKIL NTPNCALQIV ARLKNNNRQV CIDPKLKWIQ EYLEKALNKI WLYGNAETSR | 11393.88 | 7 |

In another embodiment, the sequence of an exemplary CXCL12/SDF-1 polypeptide is provided below (SEQ ID NO: 4).

```
  1 mnakvvvvlv lvltalclsd gkpvslsyrc pcrffeshva ranvkhlkil
    ntpncalqiv 61 arlknnnrqv cidpklkwiq eylekalnkg rreekvgkke kigkkkrqkk
    rkaaqkrkn
```

In one embodiment, a CXCL12 polypeptide having a molecular weight greater than about 10 kD is not 100% identical to NP_001029058.

In yet another embodiment, a CXCL12 polypeptide has at least about 85%, 90%, 95%, or 100% amino acid sequence identity to a CXCL12 isoform delta polypeptide and has chemokine or fugetaxis activity. The sequence of an exemplary CXCL12 isoform delta polypeptide is provided below (SEQ ID NO: 5):

MNAKVVVVLVLVLTALCLSDGKPVSLSYRCPCRFFESHVARANVKHLKILNTPNCALQI

VARLKNNNRQVC

IDPKLKWIQEYLEKALNNLISAAPAGKRVIAGARALHPSPPRACPTARALCEIRLWPPP

EWSWPSPGDV.

In one embodiment, a CXCL12 polypeptide having a molecular weight greater than about 10 kD is not 100% identical to the aforementioned sequence.

By "CXCL12 or SDF-1 polynucleotide" is meant a nucleic acid molecule encoding an CXCL12 or SDF-1 polypeptide.

By "CXCL12 or SDF-1 biological activity" is meant chemokine or fugetaxis activity.

By "increase in CXCL12/SDF-1" or "increase in FoxP3" is meant a detectable positive change in the level or expression of CXCL12/SDF-1 or FoxP3, respectively. Such an increase may be by 5%, 10%, 20%, 30%, or by as much as 40%, 50%, 60%, or even by as much as 75%, 80%, 90%, or 100%. Alternatively, the increase may be by 2-fold, 3-fold, 4-fold, 5-fold or even by as much as 6-fold, 7-fold, 8-fold, 9-fold, 10-fold or more.

By "portion" is meant a fragment of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100 nucleotides or amino acids.

By "severity of neoplasia" is meant the degree of pathology. The severity of a neoplasia increases, for example, as the stage or grade of the neoplasia increases.

By "specificity" is meant the percentage of subjects without a particular disease who test negative.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and most preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "neoplasia" is meant a disease that is caused by or results in inappropriately high levels of cell division, inappropriately low levels of apoptosis, or both. Examples of neoplasias include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). By "periodic" is meant at regular intervals. Periodic patient monitoring includes, for example, a schedule of tests that are administered daily, bi-weekly, bi-monthly, monthly, bi-annually, or annually.

By "reference" is meant a standard or control condition.

By "subject" is meant a mammal, including, but not limited to, a human or non-human mammal, such as a bovine, equine, canine, ovine, or feline.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

BRIEF DESCRIPTION OF THE DRAWINGS

FIGS. 1A-1R show tissue microarray (TMA) sections of normal ectocervix, normal endocervix and neoplastic cervical squamous and glandular lesions stained by ABC avidin biotin complex (ABC) immunohistochemistry (IHC)-alkaline phosphatase (AP) fast red labelling method and double immunofluorescent (IF) staining to demonstrate CXCL12% area in neoplastic and normal cervical epithelium (red). Nuclei (shown by staining) in-FIGS. 1G-L and P-R are stained with DAPI (4'-6-Diamidino-2-phenylindole); nuclei (shown by staining) in FIGS. 1A-F and M-O are stained with Meyer's haemalum. —FIGS. 1A-F show sections of normal ectocervix, cervical intraepithelial neoplasia (CIN) scale CIN1, CIN2, CIN3, microinvasive squamous carcinoma (MI) and invasive squamous cell carcinoma (INV.SCC) stained for CXCL12 (positive epithelium in red). Normal ectocervical epithelium shows no staining for CXCL12. The area of the epithelium positive for CXCL12 is confined to the basal layers in CIN1 and CIN2 lesion and it progresses in CIN3, MI and INV.SCC where it is increased and present throughout the full thickness of the neoplastic epithelium, as shown by doubleheaded arrows. FIGS. 1G-L show corresponding serial TMA sections to FIGS. 1A-1F stained with double IF for CXCL12 (red) and CD3 (green). CD3 positive T cells (green rim staining) can be seen in the stroma of FIGS. 1K and 1L (MI and INV.SCC). Green staining for CD3+ is more clearly shown after eliminating the red and blue staining of CXCL12 and nuclei, respectively (Figure Kii)(CD3+ cells are arrowed). FIG. 1M-O show images of TMA sections of normal endocervix, microinvasive squamous carcinoma (MI), invasive squamous cell carcinoma (INV.SCC), adenocarcinoma in situ AIS and invasive adenocarcinoma (ADENOCA) stained for CXCL12 using an avidin biotin complex (ABC) alkaline phosphatase (AP) fast red labelling method. There is increasing intensity of CXCL12 (red staining) in abnormal glandular epithelial cells as the lesion progressed from AIS (FIG. 1N) to ADENOCA (FIG. 1O). Normal glandular epithelium was consistently negative (FIG. 1M). Corresponding sequential serial TMA sections (FIGS. 1P-R) confirmed progressive increases in CXCL12 staining with scanty CD3 T cell infiltration (green staining) through AIS (FIG. 1Q) and ADENOCA lesions (FIG. 1R). FIG. $1Q_{ii}$ shows the green staining for CD3+ after eliminating the red and blue staining of CXCL12 and nuclei, respectively (CD3+ cells are arrowed). Bar in upper right of A=50 microns.

FIG. 2A provides boxplots of CXCL12% Area showing an increase in CXCL12% Area with increasing severity of the squamous lesion (ANOVA test p<0.001 and Linear Contrast test p<0.001; assuming unequal variances). FIG. 2B provides boxplots of CD3 cell count showing an increase in CD3 cell count with increasing severity of the neoplastic lesion (ANOVA test p=0.001 and Linear Contrast test p<0.001; assuming unequal variances). FIG. 2C provides boxplots of CXCL12% area in normal endocervix and glandular neoplastic lesions showing an increase in CXCL12% Area with increasing severity of the glandular neoplastic lesions (ANOVA test p<0.001 and Linear Contrast test p=0.005; assuming unequal variances). FIG. 2D provides boxplots of CD3 cell count in normal endocervix and glandular neoplastic lesions showing no significant difference in CD3 cell count with increasing severity of the neoplastic lesion (ANOVA test p=0.884 and Linear Contrast test p=0.603; assuming unequal variances). FIG. 2E provides a correlation of CXCL12% Area with CD3 cell count for normal ectocervix and all neoplastic squamous lesions is statistically significant (CIN1, 2, 3, MI and INV.SCC) (Pearson correlation test $p<0.005$, $r^2=0.119$). FIG. 2F shows a correlation of CXCL12% Area with CD3 cell count for normal endocervix and all glandular neoplastic lesions was not found to be significant (AIS and ADENOCA) (Pearson correlation test $p=0.36$, $r^2=0.05$).

FIGS. 3A-3F show representative TMA sections of normal ectocervix (ABC immunoperoxidase staining) showing infiltration of CD3, CD8 and FoxP3 positive lymphocytes in normal ectocervix (3A, 3C, 3E) and invasive squamous carcinoma (3B, 3D, 3F). Cell surface staining of CD4 and CD8 positive T cells and intracellular staining of FoxP3 positive T cells is shown. Scanty infiltration of positive cells is shown for normal ectocervix as compared to heavier infiltration of these cell subpopulations in neoplastic epithelium.
Bar in 3A=50 microns.

FIG. 5A shows a Western blot analysis of CXCL12 expression in cervical neoplastic samples from squamous and glandular epithelia. Samples were separated by SDS-PAGE in lanes as indicated in the key box. Positive bands corresponding to CXCL12 are observed in samples from CIN3, INV.SCC and CIN2, but are absent in samples from normal squamous epithelium and normal glandular epithelium. Lanes labelled as in inserted Key. Positive bands for β-actin are shown for all tissue derived samples in Lanes 1-8 and lane 10. FIG. 5E shows that a significant difference is demonstrated in boxplots of CXCL12% Area of HPV16+ probe negative (neg) and HPV16+ probe positive (pos) cases for pooled samples of normal endocervical and glandular neoplastic lesions ($p<0.005$). The source of the data used for the box plots 5D and E has been derived from Table 2. Bar in B=50 microns.

FIGS. 6A-6E show representative samples prepared from ThinPreps™ of normal and abnormal cervices (Pap tests) and stained for CXCL12 using ABC IHC immunoperoxidase staining method. Positively stained dyskariotic (abnormal) cells appear brown. FIG. 6A shows normal squamous cells in a Thin Prep™ slide from a Pap test that was reported negative for malignancy. Note the absence of brown stain in cytoplasm and small regular nuclei of the squamous epithelial cells (×200). FIG. 6B shows normal endocervical cells in same Thin Prep™ slide. Note the absence of brown stain and honeycomb pattern of the cell cluster which have small regular rounded nuclei (×400). FIG. 6C shows four severely dyskariotic (high grade SIL/CIN3) cells in Thin Prep™ slide from a Pap test specimen that was reported as positive for malignancy. Note positive CXCL12 staining (dark brown) cytoplasm of the dyskariotic cells. Normal squames in the same slide are negative for CXCL12 (×200). FIG. 6D shows two large dyskariotic cells from the same specimen as FIG. 6C showing positive CXCL12 staining. The large irregular nuclei (blue) which are characteristic of dyskariotic cells are clearly seen (×400). FIG. 6E shows a cluster of severely dyskariotic cells in a Thin Prep™ slide from the same specimen. Note the strong positive CXCL12 cytoplasmic staining (brown) and enlarged irregular nucleus (blue) in each abnormal cell. The few normal squames in the picture are negative for CXCL12 (×400).

DETAILED DESCRIPTION OF THE INVENTION

Figure 2A:
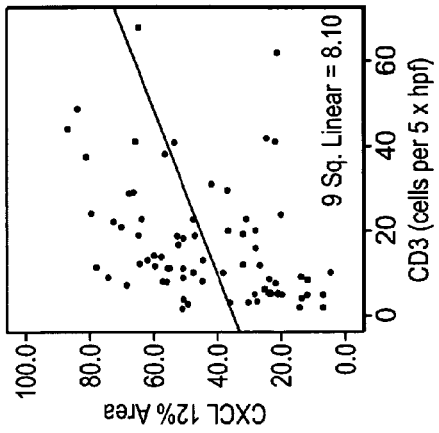
FIGS. 2A-2F are graphs. Data obtained as a result of quantitative image analysis of IF stained TMA sections of normal ectocervix and endocervix and neoplastic squamous and glandular lesions with respect to CXCL12% Area and CD3 cell count. The data are presented as boxplots (FIG. 2A-D) and as correlation graphs (FIGS. 2E and 2F).
Figure 2C:
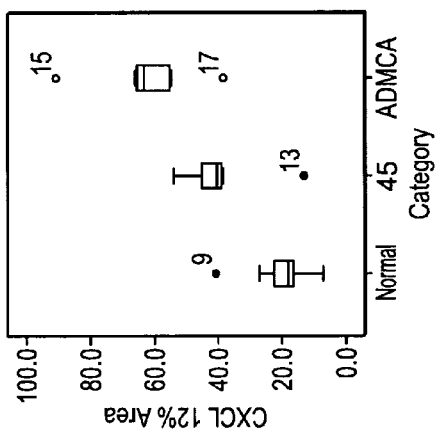
Figure 2E:
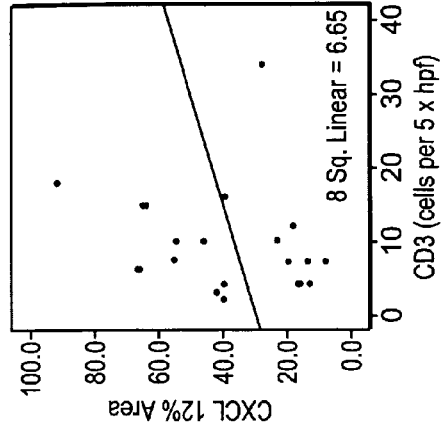
Figure 2B:
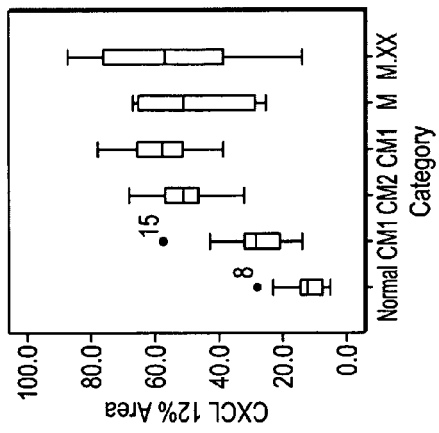

The invention features compositions and methods that are useful for screening of samples for neoplasia (e.g., ovarian, cervical, melanoma, and renal carcinomas), diagnosis of neoplasia, and assessing efficacy of the treatment of neoplasia. The invention is based, at least in part, on the discovery that a CXCL12 polypeptide having a molecular weight greater than about 10 kD is expressed in neoplastic cells (e.g., in ovarian and cervical cancer cells) and that CXCL12 expression by cervical precancerous and cancerous lesions correlated with histopathological progression, loss of immune control of the tumor and HPV infection.

Human cervical cancer is an immunogenic tumor that has a defined pattern of histopathological and clinical progression. Tumor infiltrating T cells contribute to immune control of this tumor. However the tumor dysregulates the immune response to itself through the generation of cytokines and chemokines and by its association with HPV infection. In some animal tumor models, overproduction of the chemokine, stromal cell derived factor (CXCL12) is associated with dysregulation of tumor specific immunity Surprisingly, a significant association was discovered between stage of cancer and CXCL12 expression for squamous and glandular lesions and with HPV-16+ (high risk) status of the neoplastic lesions. Cancer progression was correlated with increasing levels of FoxP3 T cell infiltration of the tumor. Of particular significance was the correlation between CXCL12 expression and FoxP3 for both squamous and glandular of neoplastic lesions. These observations were supported by ELISA and Western blotting. CXCL12 expression was found in dyskaryotic cells in Thin Prep™ cervical smears. The results reported in more detail below robustly link increased CXCL12 expression and FoxP3+-cell infiltration to HPV infection and progression of cervical cancer. It supports the detection of CXCL12 in cervical smears and biopsies as an additional biomarker for this disease.

Unexpectedly, the CXCL12 polypeptide detected by Western blot in cervical cancer had a molecular weight greater than CXCL12 (NP_001029058). The molecular weight of CXCL12 (NP_001029058) is about 8 kD. In contrast, the CXCL12 isoform associated with cervical and ovarian cancer was at least about 14-15 kD. This is the first time that an association between a CXCL12 isoform having a molecular weight greater than about 10 kD has been identified.

Accordingly, the invention provides compositions and methods for detecting and staging neoplasia (e.g., ovarian, cervical, melanoma, and renal carcinomas), for monitoring treatment efficacy, for selecting treatments appropriate for neoplasias (e.g., ovarian, cervical, melanoma, and renal carcinomas) of different stages, and for detecting a propensity for a patient to develop a neoplasia (e.g., ovarian, breast, cervical, melanoma, and renal carcinomas).

Cervical Cancer

Cervical cancer accounts for the vast majority (98.5%) of all neoplastic lesions arising in the uterine cervix. Two main forms of cervical cancer are recognized, squamous cancers (or squamous carcinoma) and glandular cancers (or adenocarcinoma). Both squamous cancers and glandular cancers have clinically and/or histologically recognizable invasive stages. They also both have histologically recognizable pre-invasive stages. The preinvasive stage of squamous carcinoma is known as cervical intraepithelial neoplasia (CIN); the preinvasive stage of glandular cancers is know as glandular intraepithelial neoplasia (GIN) or adenocarcinoma in situ. Squamous cancer also has a microinvasive stage. Mixed squamous and glandular cancers are also found in the cervix and cervical cancer may also be found in association with or mixed with other neoplastic lesions of the cervix.

Human cervical cancer is an immunogenic tumor and several tumor specific antigens have been identified in recent years. Persistent infection with high risk HPV (Types 16 and 18) has been shown to be an important risk factor for malignant transformation of the cervical epithelium. Tumor immunity in this context results from the positive recognition of tumor antigens by immature dendritic cells which subsequently migrate to draining lymph nodes which interact and activate both helper CD4+ T cells and effector antigen specific CD8+ T cells (1). Activated and targeted antigen specific cytotoxic CD8+ T cells subsequently circulate through the peripheral blood to the tumor and then selectively transmigrate into the cancer itself and kill tumor cells. Immune control of cervical cancer is therefore critically dependent on the activation and migration of tumor specific cytotoxic T cells (CTLs) into the tumor and the subsequent killing of neoplastic cells. The success of the immune response in destroying cervical cancer is thought to depend on the relationship between the kinetics of tumor growth and the efficacy of tumor specific CTLs (in balance with regulatory T cells) in infiltrating the tumor and killing neoplastic cells over time. It is well established that the magnitude of T cell infiltration within certain forms of cancer correlates with a favorable prognosis.

Tumors including cervical cancer evade immune recognition using a number of different mechanisms, including the down-regulation of major histocompatibility (MHC) class I antibodies, the immunological ignorance to tumor antigens, the lack of co-stimulatory molecules and antigen loss, or the expression of inhibitory molecules. Several studies have also shown that tumors, including cervical cancer, overexpress specific chemokines such as stromal cell derived factor 1 (SDF-1 or CXCL12) which are thought to dysregulate the immune response to the tumor. Chemokines are a superfamily of 8-11 kDa proteins found in humans which have been shown to be critical in causing directional movement of immune cells in vitro and in determining the localization of leukocytes in models of inflammatory, immune-mediated diseases and cancer. Chemokines have been shown to act as chemoattractants for leukocyte subpopulations including T cells and dendritic cells. Chemokines signal via G$\alpha$i protein coupled receptors (GPCR) on the cell surface and subsequently induce directed cell movement in response to a gradient of the chemokines.

The chemokine CXCL12, is a known T cell chemoattractant that selectively binds the receptor CXCR4. Until recently CXCL12 was thought only to have chemoattractant activity for T cells. The chemokine CXCL12 can also serve as a bidirectional cue, attracting T-cells at low concentration and repelling at high concentrations in vitro and in vivo. Certain murine models of melanoma and ovarian cancer indicate that the effect of CXCL12 on the tumor immune response is dose dependent. Low levels of CXCL12 expression result in infiltration of the tumor by T cells, delay in tumor growth and the development of a long lived tumor specific T cell mediated immune response. In contrast, high levels of CXCL12 expression result in reduced infiltration of the tumor by tumor antigen specific T cells and the suppression of anti-tumor immune responses via various mechanisms including the intratumoral accumulation of FoxP3+ suppressor T cells.

Methods for Detecting Cervical Cancer, Ovarian Cancer, and Other Neoplasias

Invasive cervical cancer can be prevented by detection of the cancer at its earliest stages. The Papanicoloau test (more commonly referred to as the PAP smear) has proved to be a valuable method of screening for preinvasive disease, limited only by the fact that it is a very labour intensive procedure and has a false negative rate for high grade neoplastic lesions of between 8-15%. A method of screening for cervical cancer which has the potential for full automation could be of value in refining the Pap test and expanding its use especially in countries where cervical cancer is rife and cervical screening is most needed.

As shown herein, immunohistochemical staining of Thin-Prep™ slides for CXCL12 indicated that this chemokine is a valuable marker which can be used for the automated analysis of cervical smears. In the histological and cytological studies presented here, CXCL12 was highly specific for dyskaryosis with clearly negative normal epithelium. This indicates that CXCL12 is useful as a diagnostic or screening tool in clinical practice. Finally, the finding of statistically significant correlations between CXCL12 expression, FoxP3+ cell infiltration and HPV infection in the progression of cervical cancer provides insight into pathogenetic mechanisms by which a viral infection may contribute to dysplastic changes in cervical epithelial and glandular cells while initiating a process by which these cells evade the immune system as a result of effector immune cell suppression through the recruitment of suppressor T cells and the overexpression of an effector T cell chemorepellent.

Given that a CXCL12 isoform having a molecular weight greater than about 10 kD has been identified in multiple neoplasias, CXCL12 can be used as a biomarker not only for cervical cancer, but for a variety of other neoplasias. CXCL12 and FoxP3, alone or in combination, are robust biomarkers for the clinical progression of neoplasia (e.g., ovarian, breast, cervical, melanoma, and renal carcinomas), which allows clinicians to assess the efficacy of cancer therapy. Accordingly, the invention provides compositions and methods of screening for CXCL12 and/or FoxP3. Importantly, these methods may be incorporated into standard cervical smear and liquid cervical cell preparations to improve the specificity and sensitivity of this form of high throughput clinical testing for cervical cancer. In addition, CXCL12 can be used in methods of neoplasia detection, including tumor and needle biopsies.

In one embodiment, the invention provides a method of monitoring treatment progress for neoplasia (e.g., ovarian, breast, cervical, melanoma, and renal carcinomas). The method includes the step of determining a level of diagnostic marker (e.g., CXCL12, FoxP3) or diagnostic measurement (e.g., screen, assay) in a subject suffering from or susceptible to a disorder or symptoms thereof associated with neoplasia (e.g., ovarian, breast, cervical, melanoma, and renal carcinomas), in which the subject has been administered a therapeutic amount of a compound sufficient to treat the disease or symptoms thereof. The level of CXCL12 or FoxP3 determined in the method can be compared to known levels of CXCL12 or FoxP3 in either healthy normal controls or in other afflicted patients to establish the subject's disease status. In preferred embodiments, a second level of CXCL12 or FoxP3 in the subject is determined at a time point later than the determination of the first level, and the two levels are compared to monitor the course of disease or the efficacy of the therapy. In certain preferred embodiments, a pre-treatment level of CXCL12 or FoxP3 in the subject is determined prior to beginning treatment according to this invention; this pre-treatment level of CXCL12 or FoxP3 can then be compared to the level of CXCL12 or FoxP3 in the subject after the treatment commences, to determine the efficacy of the treatment.

In other embodiments, SDF or FoxP3-assays are particularly helpful in determining the malignant potential of neoplasias, particularly of CIN lesions in the cervix. It is well established that CIN lesions vary in their potential for progressing to invasive cancer. At present there are no satisfactory methods of establishing the potential aggressiveness of CIN lesions. It is currently assumed that the demonstration of high risk HPV DNA in the cervix reflects the aggressiveness of a cervical lesion. However, integrated HPV16 is found in normal cervices as well as in CIN which suggests that assaying for HPV will not be useful in assessing the potential for progression of CIN lesions. In contrast, CXCL12 and FoxP3 levels correlate with CIN stage, and these levels likely correlate with HPV status, as well. CXCL12 or FoxP3 level may be used together with cervical histology and cytology to predict the neoplastic or invasive potential of a given CIN lesion. This approach will likely improve clinical management in selecting cases for invasive surgical procedures and/or for intensive monitoring. Moreover, it will minimize patient anxiety and overtreatment of many cases of CIN that are unlikely to become invasive or metastasize. Accordingly, the invention provides methods for treatment selection where a neoplasia (e.g., ovarian, breast, cervical, melanoma, and renal carcinomas) that fails to express CXCL12 and/or FoxP3 is identified as requiring less invasive treatment. A neoplasia (e.g., ovarian, breast, cervical, melanoma, and renal carcinomas) that expresses CXCL12, alone or in combination with FoxP3 is identified as requiring aggressive treatment. Aggressive treatments may include chemotherapy, radiation therapy, or surgical resection of the neoplasia.

CXCL12 or FoxP3 assays are also useful as follow-up procedures for patients who have been treated for neoplasia (e.g., ovarian, breast, cervical, melanoma, and renal carcinomas). In one embodiment, a CXCL12 and/or FoxP3 assay is used as a followup after laser ablation for CIN. These patients are currently monitored annually for at least ten years by cytology for evidence of recurrence. However, a retrospective review of these cases (Coleman & Poznansky 2006) shows that the detection of recurrence of CIN and invasive cancer may be delayed until the lesion is quite advanced because the new lesions often arises high in the endocervix and the cervical smears contain only a few cancer cells which may be overlooked by the screener. Routine assay of cytological specimens for CXCL12 or FoxP3 during the follow up period is likely to provide for early detection of recurrence and improve the prognosis for these patients.

Moreover, CXCL12 or FoxP3 is likely to be useful as a screening tool for the detection of neoplasias. In particular embodiments, CXCL12 and/or FoxP3 are likely to be useful as screening tools for the detection of cervical neoplasia in patients with no prior history of disease. Liquid based cytology (LBC) specimens are particularly useful for the immunoassay of CXCL12 and other cytokines as the cells of interest in these samples can be readily accessed for immunohistochemical evaluation. LBC had recently been approved by the FDA smear test for Pap testing. It is gaining acceptance world wide as an alternative to the conventional smear test as sample preparation is automated and the cells of interest can be clearly displayed on a microscope slide or can be processed in suspension. The results reported herein indicate that there is a clear distinction in CXCL12 expression between benign and malignant glandular epithelium. Because no clear cut cytodiagnosis is available, an CXCL12 or FoxP3 immunoassay provides a valuable improvement over currently available conventional diagnostics.

Moreover, the results reported herein further indicate that any CXCL12 or CXCL12 receptor antagonists, including small compounds (e.g., AMD3100 and other CXCR4 small molecule antagonists) and antibodies against CXCL12 or its receptor may be useful for the treatment of neoplasia (e.g., ovarian, breast, cervical, melanoma, and renal carcinomas). Such antagonists (e.g., small compounds, inhibitory CXCL12 antibodies) would likely inhibit the progression of neoplasias, including CIN lesions. For treatment of cervical cancer, the antibody could be applied topically (under colposcopic guidance) to the cervical lesion. Although HPV vaccination with high risk HPV types is currently being promoted in young girls as a preventative measure against cervical cancer, the evidence that it prevents the development of CIN or invasive cancer in the long term is limited and there is a continuing need to explore ways of inhibiting the development of neoplastic changes in the cervix. This goal could be achieved by the topical application of an anti-CXCL12 antibody that would effectively promote the proliferation of specific cytotoxic immune cells in the cervix or reverse T cell fugetaxis, thereby reducing the risk of HPV infection and epithelial cell transformation associated with these oncogenic viruses.

Increasing evidence supports the existence of elevated numbers of regulatory T cells ($T_{reg}$ cells) in solid tumors and hematologic malignancies. In solid cancers this has been shown in non-small-cell lung cancer, ovarian cancer, melanoma, gastrointestinal cancers, squamous cell carcinoma of the head and neck, and hepatocellular carcinomas. CD4+ CD25+FOXP3+ T$_{reg}$ cells have been shown to suppress tumor-specific T-cell immunity in ovarian cancer, contribute to tumor growth, and accumulate during cancer progression. Furthermore, it was shown that increased frequencies of T$_{reg}$ cells were associated with a high death hazard ratio and reduced survival in ovarian cancer. Without being bound to a particular theory, the specific recruitment of T$_{reg}$ cells to tumors might represent a mechanism by which tumors may foster immune privilege.

An inhibitory FoxP3 antibody or FoxP3 inhibitory nucleic acid molecule would likely inhibit the progression of neoplasias, including CIN lesions. Such inhibitors could be applied topically (under colposcopic guidance) to the cervical lesion.

Types of Biological Samples

The level of CXCL12 or FoxP3 in a neoplasia (e.g., ovarian, breast, cervical, melanoma, and renal carcinomas) can be measured in different types of biologic samples. In one embodiment, the biologic sample is a tissue sample that includes cervical tissue cells, for example, a tissue sample obtained during colposcopy. Cervical tissue is obtained, for example, from a biopsy of the cervix. In another embodiment, the biologic sample is a cellular sample obtained by scraping or abrading the cervix during a pelvic examination. Cell samples obtained are then put onto a microscope slide or into a liquid medium for histochemical, cytological, or immunocytochemical evaluation by a diagnostician or in an automated diagnostic setting. In other embodiments, the sample is a needle or tumor biopsy. In still other embodiments, the sample is a biological fluid (e.g., blood, saliva, vaginal secretion, semen, spinal fluid).

Diagnostic Assays

Assays of CXCL12 and/or FoxP3 are useful for the identification of neoplasias, including CIN and for CIN staging (e.g., distinguishing between the preinvasive stages of CIN 1,2, and micro and invasive stages of squamous cervical cancer). The CIN (cervical intraepithelial neoplasia) scale is used for grading cervical neoplasia. The CIN scale has three distinct grades. In CIN1 (Grade I) describes cervical tissue that exhibits mild dysplasia, or abnormal cell growth and the dysplasia is confined to the basal ⅓ of the epithelium. In CIN2 (Grade II), cervical tissue exhibits moderate dysplasia, and the dysplasia is confined to the basal ⅔ of the epithelium. In CIN3 (Grade III), cervical tissue exhibits severe dysplasia, and the dysplasia spans the full thickness of the epithelium. This lesion may also be referred to as cervical carcinoma in situ.

Selection of a Treatment Method

The management and treatment of patients with cervical cancer depends on several factors including the stage of the disease at the time of diagnosis. After a subject is diagnosed as having a cervical neoplasia, a method of treatment is selected. In cervical cancer, for example, a number of standard treatment regimens are available. The stage of CIN as indicated by the level of CXCL12 and/or FoxP3 in a cervical lesion is used in selecting a treatment method. As described herein, the level of CXCL12 and/or FoxP3 can be used to assist in the management and treatment of patients with cervical cancer because the level of CXCL12 and/or FoxP3 correlates with the stage of the disease at diagnosis, i.e., whether it is preinvasive or invasive. The level of CXCL12 and/or FoxP3 can be particularly helpful in the management of preinvasive cancer because the higher grades of CIN (i.e., CIN2 or CIN3) express CXCL12 and/or FoxP3 more strongly than CIN1.

In one embodiment, cervical neoplasias having lower CXCL12 levels (i.e., lower than 1-3-fold increase relative to levels found in normal cervical tissue) are treated less aggressively (e.g., local excision, local radiotherapy, local delivery of an anti-CXCL12 agent or CXCL12 receptor antagonist) than a cervical neoplasia having higher CXCL12 levels (i.e., higher than 3-5 fold, or even 10-fold, increase relative to levels found in normal cervical tissue). In another embodiment, the level of CXCL12 and/or FoxP3 in cervical neoplasia is correlated with a clinical outcome using statistical methods to determine the aggressiveness of the neoplasia. CXCL12 levels that correlate with poor clinical outcomes, such as metastasis or death, are identified as aggressive cervical neoplasias. CXCL12 and/or FoxP3 levels that correlate with good clinical outcomes are identified as less aggressive cervical neoplasias.

Neoplasias having minimally increased CXCL12 and/or FoxP3 levels are likely to be susceptible to less aggressive treatment methods. Such treatment methods are preferred because they lack the toxicity and adverse side effects associated with some more aggressive treatments. Less aggressive treatment methods include, for example, cancer surveillance, which involves periodic patient monitoring using diagnostic assays of the invention, alone or in combination, with cervical smear, cone biopsy, or colposcopy. Cancer surveillance is selected when diagnostic assays indicate that the adverse effects of treatment are likely to outweigh therapeutic benefits. Less aggressive treatments also include local excision, loop electrical excision procedure (LEEP), local radiotherapy, trachelectomy, hormonal therapy, local delivery (e.g., topical delivery) of an anti-CXCL12 agent, CXCL12 inhibitory nucleic acid molecule, or CXCL12 receptor antagonist, or local delivery (e.g., topical delivery) of an anti-FoxP3 agent, FoxP3 inhibitory nucleic acid molecule, or FoxP3 receptor antagonist.

Cervical neoplasias having higher levels of CXCL12 indicate that aggressive treatment methods are appropriate. When methods of the invention indicate that a cervical neoplasia is or has a propensity to become invasive, for example, an aggressive method of treatment should be selected. Aggressive therapeutic regimens typically include one or more of the following therapies: hysterectomy, radiation therapy, and chemotherapy.

Patient Monitoring

The diagnostic methods of the invention are also useful for monitoring the course of neoplasia (e.g., ovarian, breast, cervical, melanoma, and renal carcinomas) in a patient or for assessing the efficacy of a therapeutic regimen. In one embodiment, the diagnostic methods of the invention are used periodically to monitor the levels of CXCL12, FoxP3, or both. In one example, the cervical neoplasia is characterized using a diagnostic assay of the invention prior to administering therapy. This assay provides a baseline that describes the level of CXCL12 or FoxP3 expression present in the cervical neoplasia prior to treatment. Additional diagnostic assays are administered during the course of therapy to monitor the efficacy of a selected therapeutic regimen. A therapy is identified as efficacious when a diagnostic assay of the invention detects a decrease in CXCL12 or FoxP3 levels relative to the baseline level of CXCL12 or FoxP3 expression.

Kits

The invention also provides kits for the diagnosis or monitoring of a neoplasia (e.g., ovarian, cervical, melanoma, and renal carcinomas) in a biological sample obtained from a subject. In various embodiments, the kit includes at least one reagent capable of detecting CXCL12 or FoxP3 protein, together with instructions for using the primer or probe to identify a neoplasia. In one embodiment, the kit further comprises an anti-CXCL12 or FoxP3 antibody, or fragments thereof. In yet another embodiment, the kit further comprises a detectable probe. In yet another embodiment, the kit further comprises a pair of primers capable of detecting a reference comprising CXCL12 or FoxP3. In yet other embodiments, the kit comprises a sterile container which contains the primer or probe; such containers can be boxes, ampoules, bottles, vials, tubes, bags, pouches, blister-packs, or other suitable container form known in the art. Such containers can be made of plastic, glass, laminated paper, metal foil, or other materials suitable for holding nucleic acids, polypeptides, or biomolecules. The instructions will generally include information about the use of the reagents or probes described herein and their use in diagnosing cervical neoplasia. Preferably, the kit further comprises any one or more of the reagents described in the diagnostic assays described herein. In other embodiments, the instructions include at least one of the following: description of the reagent or probe; methods for using the enclosed materials for the diagnosis of cervical neoplasia; precautions; warnings; indications; clinical or research studies; and/or references. The instructions may be printed directly on the container (when present), or as a label applied to the container, or as a separate sheet, pamphlet, card, or folder supplied in or with the container.

Screening Assays

As reported herein, as the stage of a neoplasia (e.g., ovarian, breast, cervical, melanoma, and renal carcinomas) increases, levels of FoxP3-positive T cells infiltrating the tumor also increased. Accordingly, the invention provides methods for treating cancer by reducing FoxP3 biological activity or expression. Virtually any agent that specifically binds FoxP3 or that reduces FoxP3 biological activity (e.g., tumor infiltration or immunoregulatory function) may be employed in the methods of the invention. In other embodiments, the assay identifies an agent that binds to a CXCL12 isoform having a molecular weight greater than about 10 kD, but fails to bind or binds at a reduced lever to CXCL12 polypeptides having a molecular weight less than about 10 kD.

Methods of the invention are useful for the high-throughput low-cost screening of candidate agents that reduce FoxP3 or CXCL12 isoform biological activity or expression. A candidate agent that specifically binds to FoxP3 and reduces FoxP3 biological activity is useful for the treatment of a cervical neoplasia. One skilled in the art appreciates that the effects of a candidate agent on a cell is typically compared to a corresponding control cell not contacted with the candidate agent. Thus, the screening methods include comparing level or biological activity of FoxP3 in a T cell contacted by a candidate agent to the level or biological activity of FoxP3 in an untreated control cell. In other embodiments, the method provides for the identification of agents that reduce FoxP3 positive T cell function, such as cells that reduce T cell chemotaxis or fugetaxis.

In other embodiments, the expression or activity of FoxP3 or a CXCL12 isoform in a cell treated with a candidate agent is compared to untreated control samples to identify a candidate compound that reduces the expression or activity of FOXP3 or a CXCL12 isoform in the contacted cell. Polypeptide expression or activity can be compared by procedures well known in the art, such as Western blotting, flow cytometry, immunocytochemistry, immunohistochemical staining, binding to magnetic and/or FOXP3 or a CXCL12 isoform-specific antibody-coated beads, in situ hybridization, fluorescence in situ hybridization (FISH), ELISA, microarray analysis, RT-PCR, Northern blotting, or colorimetric assays, such as the Bradford Assay and Lowry Assay.

In one working example, one or more candidate agents are added at varying concentrations to culture medium containing a FoxP3-positive T cell. An agent that reduces the expression of a FOXP3 polypeptide expressed in the cell is considered useful in the invention; such an agent may be used, for example, as a therapeutic to prevent, delay, ameliorate, stabilize, or treat an neoplastic disease or disorder characterized by increased infiltration of FoxP3 positive T cells in the tumor. Once identified, agents of the invention (e.g., agents that specifically bind to and/or inhibit FOXP3) may be used to treat neoplasia in a patient in need thereof.

If one embodiment, the effect of a candidate agent may, in the alternative, be measured at the level of FOXP3 polypeptide or a CXCL12 isoform production using the same general approach and standard immunological techniques, such as Western blotting or immunoprecipitation with an antibody specific for FOXP3 or a CXCL12 isoform. For example, immunoassays may be used to detect or monitor the expression of FOXP3 in a T cell or other mammalian immunoresponsive cell. In one embodiment, the invention identifies a polyclonal or monoclonal antibody (produced as described herein) that is capable of binding to and inhibiting a FOXP3 polypeptide or a CXCL12 isoform. A compound that reduces the expression or activity of a FOXP3 polypeptide or a CXCL12 isoform is considered particularly useful. Again, such a molecule may be used, for example, as a therapeutic to prevent or treat a neoplasia.

Alternatively, or in addition, candidate compounds may be identified by first assaying those that specifically bind to and inhibit a FOXP3 polypeptide or a CXCL12 isoform of the invention and subsequently testing their effect on neoplastic cell proliferation. In one embodiment, the efficacy of a candidate agent is dependent upon its ability to interact with the FOXP3 polypeptide or a CXCL12 isoform. Such an interaction can be readily assayed using any number of standard binding techniques and functional assays (e.g., those described in Ausubel et al., supra). For example, a candidate compound may be tested in vitro for interaction and binding with a FOXP3 polypeptide or a CXCL12 isoform. Potential FOXP3 or a CXCL12 isoform antagonists include organic molecules, peptides, peptide mimetics, polypeptides, nucleic acid ligands, aptamers, and antibodies that bind to a FOXP3 polypeptide and stimulate its activity.

In one particular example, a candidate compound that binds to a FOXP3 polypeptide or a CXCL12 isoform may be identified using a chromatography-based technique. For example, a recombinant FOXP3 polypeptide of the invention may be purified by standard techniques from cells engineered to express the polypeptide, or may be chemically synthesized, once purified the peptide is immobilized on a column. A solution of candidate agents is then passed through the column, and an agent that specifically binds the FOXP3 polypeptide or a CXCL12 isoform or a fragment thereof is identified on the basis of its ability to bind to FOXP3 polypeptide or a CXCL12 isoform and to be immobilized on the column. To isolate the agent, the column is washed to remove non-specifically bound molecules, and the agent of interest is then released from the column and collected. Agents isolated by this method (or any other appropriate method) may, if desired, be further purified (e.g., by high performance liquid chromatography). In addition, these candidate agents may be tested for their ability to inhibit FoxP3 or a CXCL12 isoform or to inhibit the infiltration of a solid tumor with a FoxP3-positive T cell (e.g., as described herein). Agents isolated by this approach may also be used, for example, as therapeutics to treat or prevent neoplasia. Compounds that are identified as binding to a FOXP3 polypeptide or a CXCL12 isoform with an affinity constant less than or equal to 1 nM, 5 nM, 10 nM, 100 nM, 1 mM or 10 mM are considered particularly useful in the invention.

Such agents may be used, for example, as therapeutics to treat a neoplasia (e.g., ovarian, breast, cervical, melanoma, and renal carcinomas). Optionally, agents identified in any of the above-described assays may be confirmed as useful in conferring protection against the development of a neoplasia (e.g., cervical or ovarian cancer) in any standard animal model and, if successful, may be used as anti-neoplasia therapeutics.

Test Compounds and Extracts

In general, FOXP3 or CXCL12 isoform antagonists (e.g., agents that specifically bind and inhibit the biological activity or expression of a FOXP3 polypeptide or a CXCL12 isoform) are identified from large libraries of natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Agents used in screens may include known those known as therapeutics for the treatment of neoplasia. Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as the modification of existing polypeptides.

Libraries of natural polypeptides in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Such polypeptides can be modified to include a protein transduction domain using methods known in the art and described herein. In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound is readily modified using standard chemical, physical, or biochemical methods.

Numerous methods are also available for generating random or directed synthesis (e.g., semi-synthesis or total synthesis) of any number of polypeptides, chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Libraries of compounds may be presented in solution (e.g., Houghten, *Biotechniques* 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222:301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to have FOXP3 binding and/or stimulating activity further fractionation of the positive lead extract is necessary to isolate molecular constituents responsible for the observed effect. Thus, the goal of the extraction, fractionation, and purification process is the careful characterization and identification of a chemical entity within the crude extract that inhibits. Methods of fractionation and purification of such heterogenous extracts are known in the art. If desired, compounds shown to be useful as therapeutics are chemically modified according to methods known in the art.

Therapeutic Methods

Agents identified as binding and/or inhibiting a FOXP3 polypeptide or a CXCL12 isoform are useful for preventing or ameliorating a neoplastic disease characterized by increased expression of a CXCL12 isoform having a molecular weight greater than about 10 kD or having tumor infiltration by FoxP3-positive T cells. In one therapeutic approach, an agent identified as described herein is administered to the site of a potential or actual disease-affected tissue or is administered systemically. The dosage of the administered agent depends on a number of factors, including the size and health of the individual patient. Additionally, agents which reduce levels of FoxP3-positive T cells (e.g., cyclophosphamide) are useful for preventing or ameliorating a neoplastic disease characterized by tumor infiltration by FoxP3-positive T cells. For any particular subject, the specific dosage regimes should be adjusted over time according to the individual need and the professional judgement of the person administering or supervising the administration of the compositions.

Pharmaceutical Therapeutics

The invention provides a simple means for identifying compositions (including nucleic acids, peptides, small molecule inhibitors, and monoclonal antibodies) capable of binding to and inhibiting FOXP3 or a CXCL12 isoform or acting as therapeutics for the treatment or prevention of a neoplasia. Accordingly, a chemical entity discovered to have medicinal value using the methods described herein is useful as a drug or as information for structural modification of existing compounds, e.g., by rational drug design.

For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, interperitoneally, intraperitoneally ie between the layers of the peritoneal lining, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia. Generally, amounts will be in the range of those used for other agents used in the treatment of other diseases associated neoplasia, although in certain instances lower amounts will be needed because of the increased specificity of the compound. A compound is administered at a dosage that inhibits FOXP3 as determined by a method known to one skilled in the art, or using any that assay that measures the expression or the biological activity of a FOXP3 polypeptide or a CXCL12 isoform.

Formulation of Pharmaceutical Compositions

The administration of a compound for the treatment of neoplasia (e.g., ovarian, cervical, melanoma, and renal carcinomas) may be by any suitable means that results in a concentration of the therapeutic that, combined with other components, is effective in ameliorating, reducing, or stabilizing neoplasia. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target neoplasia by using carriers or chemical derivatives to deliver the therapeutic agent to a particular cell type (e.g., T cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates neoplasia, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug may be incorporated in biocompatible carriers, liposomes, nanoparticles, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Solid Dosage Forms for Oral Use

Formulations for oral use include tablets containing the active ingredient(s) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

The solid tablet compositions may include a coating adapted to protect the composition from unwanted chemical changes, (e.g., chemical degradation prior to the release of the active a anti-neoplasia therapeutic substance). The coating may be applied on the solid dosage form in a similar manner as that described in Encyclopedia of Pharmaceutical Technology, supra.

At least two anti-neoplasia therapeutic may be mixed together in the tablet, or may be partitioned. In one example, the first active anti-neoplasia therapeutic is contained on the inside of the tablet, and the second active anti-neoplasia therapeutic is on the outside, such that a substantial portion of the second active anti-neoplasia therapeutic is released prior to the release of the first active anti-neoplasia therapeutic.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use may, e.g., be constructed to release the anti-neoplasia therapeutic by controlling the dissolution and/or the diffusion of the active substance. Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more therapeutic compounds may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the compound(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Antibodies

Antibodies that selectively bind CXCL12 (e.g., an antibody that specifically binds a CXCL12 isoform having a molecular weight greater than about 10 kD) or FoxP3 are useful in the methods of the invention. Methods of preparing antibodies are well known to those of ordinary skill in the science of immunology. As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')$_2$, and Fab. F(ab')$_2$, and Fab fragments that lack the Fc fragment of intact antibody, clear more rapidly from the circulation, and may have less non-specific tissue binding of an intact antibody (Wahl et al., *J. Nucl. Med.* 24:316-325 (1983). The antibodies of the invention comprise whole native antibodies, bispecific antibodies; chimeric antibodies; Fab, Fab', single chain V region fragments (scFv), fusion polypeptides, and unconventional antibodies.

Unconventional antibodies include, but are not limited to, nanobodies, linear antibodies (Zapata et al., Protein Eng. 8(10): 1057-1062, 1995), single domain antibodies, single chain antibodies, and antibodies having multiple valencies (e.g., diabodies, tribodies, tetrabodies, and pentabodies). Nanobodies are the smallest fragments of naturally occurring heavy-chain antibodies that have evolved to be fully functional in the absence of a light chain. Nanobodies have the affinity and specificity of conventional antibodies although they are only half of the size of a single chain Fv fragment. The consequence of this unique structure, combined with their extreme stability and a high degree of homology with human antibody frameworks, is that nanobodies can bind therapeutic targets not accessible to conventional antibodies. Recombinant antibody fragments with multiple valencies provide high binding avidity and unique targeting specificity to cancer cells. These multimeric scFvs (e.g., diabodies, tetrabodies) offer an improvement over the parent antibody since small molecules of ~60-100 kDa in size provide faster blood clearance and rapid tissue uptake See Power et al., (Generation of recombinant multimeric antibody fragments for tumor diagnosis and therapy. Methods Mol Biol, 207, 335-50, 2003); and Wu et al. (Anti-carcinoembryonic antigen (CEA) diabody for rapid tumor targeting and imaging. Tumor Targeting, 4, 47-58, 1999).

Various techniques for making and unconventional antibodies have been described. Bispecific antibodies produced using leucine zippers are described by Kostelny et al. (J. Immunol. 148(5):1547-1553, 1992). Diabody technology is described by Hollinger et al. (Proc. Natl. Acad. Sci. USA 90:6444-6448, 1993). Another strategy for making bispecific antibody fragments by the use of single-chain Fv (sFv) diners is described by Gruber et al. (J. Immunol. 152:5368, 1994). Trispecific antibodies are described by Tutt et al. (J. Immunol. 147:60, 1991). Single chain Fv polypeptide antibodies include a covalently linked $V_H::V_L$ heterodimer which can be expressed from a nucleic acid including $V_H$- and $V_L$-encoding sequences either joined directly or joined by a peptide-encoding linker as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754.

In one embodiment, an antibody that binds CXCL12 or FoxP3 is monoclonal. Alternatively, the anti-CXCL12 or FoxP3 antibody is a polyclonal antibody. The preparation and use of polyclonal antibodies are also known the skilled artisan. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')$_2$" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab' fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Antibodies can be made by any of the methods known in the art utilizing chemokines, or immunogenic fragments thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding CXCL12, FoxP3 or immunogenic fragments thereof, can be provided to the host in a delivery vehicle that is taken up by immune cells of the host. The cells will in turn express the receptor on the cell surface generating an immunogenic response in the host. Alternatively, nucleic acid sequences encoding CXCL12, FoxP3 or immunogenic fragments thereof, can be expressed in cells in vitro, followed by isolation of the receptor and administration of the receptor to a suitable host in which antibodies are raised.

Alternatively, antibodies against CXCL12 or FoxP3 may, if desired, be derived from an antibody phage display library. A bacteriophage is capable of infecting and reproducing within bacteria, which can be engineered, when combined with human antibody genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface.

Antibodies made by any method known in the art can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

Monoclonal antibodies (Mabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

Inhibitory Nucleic Acids

Inhibitory nucleic acid molecules are those oligonucleotides that selectively inhibit the expression or activity of a FoxP3 polypeptide or a CXCL12 isoform or nucleic acid molecule. Such oligonucleotides include single and double stranded nucleic acid molecules (e.g., DNA, RNA, and analogs thereof) that are complementary to or that bind a nucleic acid molecule that encodes a a FoxP3 polypeptide or a CXCL12 isoform polypeptide (e.g., antisense molecules, RNAi, siRNA, shRNA) as well as nucleic acid molecules that bind directly to a FoxP3 polypeptide or a CXCL12 isoform polypeptide to modulate its biological activity (e.g., aptamers).

siRNA

Short twenty-one to twenty-five nucleotide double-stranded RNAs are effective at down-regulating gene expression (Zamore et al., Cell 101: 25-33; Elbashir et al., Nature 411: 494-498, 2001, hereby incorporated by reference). The therapeutic effectiveness of an siRNA approach in mammals was demonstrated in vivo by McCaffrey et al. (Nature 418: 38-39.2002).

Given the sequence of a target gene, siRNAs may be designed to inactivate that gene. Such siRNAs, for example, could be administered directly to an affected tissue, or administered systemically. The nucleic acid sequence of a FoxP3 polypeptide gene can be used to design small interfering RNAs (siRNAs). The 21 to 25 nucleotide siRNAs may be used, for example, as therapeutics to treat a neoplastic disease or disorder.

The inhibitory nucleic acid molecules of the present invention may be employed as double-stranded RNAs for RNA interference (RNAi)-mediated knock-down of FoxP3 polypeptide expression. In one embodiment, FoxP3 polypeptide or a CXCL12 isoform expression is reduced in a neoplastic cell. RNAi is a method for decreasing the cellular expression of specific proteins of interest (reviewed in Tuschl, Chembiochem 2:239-245, 2001; Sharp, Genes & Devel. 15:485-490, 2000; Hutvagner and Zamore, Curr. Opin. Genet. Devel. 12:225-232, 2002; and Hannon, Nature 418: 244-251, 2002). The introduction of siRNAs into cells either by transfection of dsRNAs or through expression of siRNAs using a plasmid-based expression system is increasingly being used to create loss-of-function phenotypes in mammalian cells.

Ribozymes

Catalytic RNA molecules or ribozymes that include an antisense FoxP3 or a CXCL12 isoform sequence of the present invention can be used to inhibit expression of a FoxP3 nucleic acid molecule or polypeptide in vivo. The inclusion of ribozyme sequences within antisense RNAs confers RNA-cleaving activity upon them, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference.

Accordingly, the invention also features a catalytic RNA molecule that includes, in the binding arm, an antisense RNA having between eight and nineteen consecutive nucleobases. In preferred embodiments of this invention, the catalytic nucleic acid molecule is formed in a hammerhead or hairpin motif Examples of such hammerhead motifs are described by Rossi et al., Aids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. These specific motifs are not limiting in the invention and those skilled in the art will recognize that all that is important in an enzymatic nucleic acid molecule of this invention is that it has a specific substrate binding site which is complementary to one or more of the target gene RNA regions, and that it has nucleotide sequences within or surrounding that substrate binding site which impart an RNA cleaving activity to the molecule.

shRNA

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). In one embodiment of the invention, the shRNA molecule is made that includes between eight and twenty-one consecutive nucleobases of a FoxP3 gene. For expression of shRNAs within cells, plasmid vectors containing either the polymerase III H1-RNA or U6 promoter, a cloning site for the stem-looped RNA insert, and a 4-5-thymidine transcription termination signal can be employed (e.g., pGeneClip Neomycin Vector; Promega Corporation). The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs.

For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

Oligonucleotides and Other Nucleobase Oligomers

At least two types of oligonucleotides induce the cleavage of RNA by RNase H: polydeoxynucleotides with phosphodiester (PO) or phosphorothioate (PS) linkages. Although 2'-OMe-RNA sequences exhibit a high affinity for RNA targets, these sequences are not substrates for RNase H. A desirable oligonucleotide is one based on 2'-modified oligonucleotides containing oligodeoxynucleotide gaps with some or all internucleotide linkages modified to phosphorothioates for nuclease resistance. The presence of methylphosphonate modifications increases the affinity of the oligonucleotide for its target RNA and thus reduces the $IC_{50}$. This modification also increases the nuclease resistance of the modified oligonucleotide. It is understood that the methods and reagents of the present invention may be used in conjunction with any technologies that may be developed, including covalently-closed multiple antisense (CMAS) oligonucleotides (Moon et al., Biochem J. 346:295-303, 2000; PCT Publication No. WO 00/61595), ribbon-type antisense (RiAS) oligonucleotides (Moon et al., J. Biol. Chem. 275:4647-4653, 2000; PCT Publication No. WO 00/61595), and large circular antisense oligonucleotides (U.S. Patent Application Publication No. US 2002/0168631 A1).

As is known in the art, a nucleoside is a nucleobase-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside.

For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure; open linear structures are generally preferred. Within the oligonucleotide structure, the phosphate groups are commonly referred to as forming the backbone of the oligonucleotide. The normal linkage or backbone of RNA and DNA is a 3' to 5' phosphodiester linkage.

Specific examples of preferred nucleobase oligomers useful in this invention include oligonucleotides containing modified backbones or non-natural internucleoside linkages. As defined in this specification, nucleobase oligomers having modified backbones include those that retain a phosphorus atom in the backbone and those that do not have a phosphorus atom in the backbone. For the purposes of this specification, modified oligonucleotides that do not have a phosphorus atom in their internucleoside backbone are also considered to be nucleobase oligomers.

Nucleobase oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriest-ers, and boranophosphates having normal 3'-5' linkages, 2'-5' linked analogs of these, and those having inverted polarity, wherein the adjacent pairs of nucleoside units are linked 3'-5' to 5'-3' or 2'-5' to 5'-2'. Various salts, mixed salts and free acid forms are also included. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Nucleobase oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other nucleobase oligomers, both the sugar and the internucleoside linkage, i.e., the backbone, are replaced with novel groups. The nucleobase units are maintained for hybridization with a nucleic acid molecule encoding a FoxP3 polypeptide. One such nucleobase oligomer, is referred to as a Peptide Nucleic Acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Methods for making and using these nucleobase oligomers are described, for example, in "Peptide Nucleic Acids: Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

In particular embodiments of the invention, the nucleobase oligomers have phosphorothioate backbones and nucleosides with heteroatom backbones, and in particular —$CH_2$—, NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$—, and —O—N($CH_3$)—$CH_2$—$CH_2$—. In other embodiments, the oligonucleotides have morpholino backbone structures described in U.S. Pat. No. 5,034,506.

Nucleobase oligomers may also contain one or more substituted sugar moieties. Nucleobase oligomers comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)nON[(CH_2)_nCH_3)]_2$, where n and m are from 1 to about 10. Other preferred nucleobase oligomers include one of the following at the 2' position: $C_1$ to $C_{10}$ lower alkyl, substituted lower alkyl, alkaryl, aralkyl, O-alkaryl, or O-aralkyl, SH, $SCH_3$, OCN, Cl, Br, CN, $CF_3$, $OCF_3$, $SOCH_3$, $SO_2CH_3$, $ONO_2$, $NO_2$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of a nucleobase oligomer, or a group for improving the pharmacodynamic properties of an nucleobase oligomer, and other substituents having similar properties. Preferred modifications are 2'-O-methyl and 2'-methoxyethoxy (2'-O—$CH_2CH_2OCH_3$, also known as 2'-O-(2-methoxyethyl) or 2'-MOE). Another desirable modification is 2'-dimethylaminooxyethoxy (i.e., $O(CH_2)_2ON(CH_3)_2$), also known as 2'-DMAOE. Other modifications include, 2'-aminopropoxy (2'-$OCH_2CH_2CH_2NH_2$) and 2'-fluoro (2'-F). Similar modifications may also be made at other positions on an oligonucleotide or other nucleobase oligomer, particularly the 3' position of the sugar on the 3' terminal nucleotide or in 2'-5' linked oligonucleotides and the 5' position of 5' terminal nucleotide. Nucleobase oligomers may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053;

5,639,873; 5,646,265; 5,658,873; 5,670,633; and 5,700,920, each of which is herein incorporated by reference in its entirety.

Nucleobase oligomers may also include nucleobase modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine; 2-propyl and other alkyl derivatives of adenine and guanine; 2-thiouracil, 2-thiothymine and 2-thiocytosine; 5-halouracil and cytosine; 5-propynyl uracil and cytosine; 6-azo uracil, cytosine and thymine; 5-uracil (pseudouracil); 4-thiouracil; 8-halo, 8-amino, 8-thiol, 8-thioalkyl, 8-hydroxyl and other 8-substituted adenines and guanines; 5-halo (e.g., 5-bromo), 5-trifluoromethyl and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of an antisense oligonucleotide of the invention. These include 5-substituted pyrimidines, 6-azapyrimidines, and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., eds., Antisense Research and Applications, CRC Press, Boca Raton, 1993, pp. 276-278) and are desirable base substitutions, even more particularly when combined with 2'-O-methoxyethyl or 2'-O-methyl sugar modifications. Representative United States patents that teach the preparation of certain of the above noted modified nucleobases as well as other modified nucleobases include U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,750,692, each of which is herein incorporated by reference.

Another modification of a nucleobase oligomer of the invention involves chemically linking to the nucleobase oligomer one or more moieties or conjugates that enhance the activity, cellular distribution, or cellular uptake of the oligonucleotide. Such moieties include but are not limited to lipid moieties such as a cholesterol moiety (Letsinger et al., Proc. Natl. Acad. Sci. USA, 86:6553-6556, 1989), cholic acid (Manoharan et al., Bioorg. Med. Chem. Let, 4:1053-1060, 1994), a thioether, e.g., hexyl-5-tritylthiol (Manoharan et al., Ann. N.Y. Acad. Sci., 660:306-309, 1992; Manoharan et al., Bioorg. Med. Chem. Let., 3:2765-2770, 1993), a thiocholesterol (Oberhauser et al., Nucl. Acids Res., 20:533-538: 1992), an aliphatic chain, e.g., dodecandiol or undecyl residues (Saison-Behmoaras et al., EMBO J., 10:1111-1118, 1991; Kabanov et al., FEBS Lett., 259:327-330, 1990; Svinarchuk et al., Biochimie, 75:49-54, 1993), a phospholipid, e.g., dihexadecyl-rac-glycerol or triethylammonium 1,2-di-O-hexadecyl-rac-glycero-3-H-phosphonate (Manoharan et al., Tetrahedron Lett., 36:3651-3654, 1995; Shea et al., Nucl. Acids Res., 18:3777-3783, 1990), a polyamine or a polyethylene glycol chain (Manoharan et al., Nucleosides & Nucleotides, 14:969-973, 1995), or adamantane acetic acid (Manoharan et al., Tetrahedron Lett., 36:3651-3654, 1995), a palmityl moiety (Mishra et al., Biochim. Biophys. Acta, 1264:229-237, 1995), or an octadecylamine or hexylamino-carbonyl-oxycholesterol moiety (Crooke et al., J. Pharmacol. Exp. Ther., 277:923-937, 1996. Representative United States patents that teach the preparation of such nucleobase oligomer conjugates include U.S. Pat. Nos. 4,587,044; 4,605,735; 4,667,025; 4,762,779; 4,789,737; 4,824,941; 4,828,979; 4,835,263; 4,876,335; 4,904,582; 4,948,882; 4,958,013; 5,082,830; 5,109,124; 5,112,963; 5,118,802; 5,138,045; 5,214,136; 5,218,105; 5,245,022; 5,254,469; 5,258,506; 5,262,536; 5,272,250; 5,292,873; 5,317,098; 5,371,241; 5,391,723; 5,414,077; 5,416,203, 5,451,463; 5,486,603; 5,510,475; 5,512,439; 5,512,667; 5,514,785; 5,525,465; 5,541,313; 5,545,730; 5,552,538; 5,565,552; 5,567,810; 5,574,142; 5,578,717; 5,578,718; 5,580,731; 5,585,481; 5,587,371; 5,591,584; 5,595,726; 5,597,696; 5,599,923; 5,599,928; 5,608,046; and 5,688,941, each of which is herein incorporated by reference.

The present invention also includes nucleobase oligomers that are chimeric compounds. "Chimeric" nucleobase oligomers are nucleobase oligomers, particularly oligonucleotides, that contain two or more chemically distinct regions, each made up of at least one monomer unit, i.e., a nucleotide in the case of an oligonucleotide. These nucleobase oligomers typically contain at least one region where the nucleobase oligomer is modified to confer, upon the nucleobase oligomer, increased resistance to nuclease degradation, increased cellular uptake, and/or increased binding affinity for the target nucleic acid. An additional region of the nucleobase oligomer may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of nucleobase oligomer inhibition of gene expression. Consequently, comparable results can often be obtained with shorter nucleobase oligomers when chimeric nucleobase oligomers are used, compared to phosphorothioate deoxyoligonucleotides hybridizing to the same target region.

Chimeric nucleobase oligomers of the invention may be formed as composite structures of two or more nucleobase oligomers as described above. Such nucleobase oligomers, when oligonucleotides, have also been referred to in the art as hybrids or gapmers. Representative United States patents that teach the preparation of such hybrid structures include U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The nucleobase oligomers used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The nucleobase oligomers of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Naked inhibitory nucleic acid molecules, or analogs thereof, are capable of entering mammalian cells and inhibiting expression of a gene of interest. Nonetheless, it may be desirable to utilize a formulation that aids in the delivery of oligonucleotides or other nucleobase oligomers to cells (see, e.g., U.S. Pat. Nos. 5,656,611, 5,753,613, 5,785,992, 6,120, 798, 6,221,959, 6,346,613, and 6,353,055, each of which is hereby incorporated by reference).

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

It should be appreciated that the invention should not be construed to be limited to the examples that are now described; rather, the invention should be construed to include any and all applications provided herein and all equivalent variations within the skill of the ordinary artisan.

EXAMPLES

Example 1

CXCL12 was Expressed in Neoplastic Lesions

383 TMA tissue cores (prepared from 83 positive cases and 24 controls) stained by the ABC (AP) method using Fast red chromogen were assessed manually by light microscopy for CXCL12 expression. The antigen was expressed in the epithelium and stroma of neoplastic squamous and glandular lesions. The location of the epithelial staining was clearly intracellular and well defined whereas stromal staining was generally extracellular and diffuse. An increase in intensity and distribution of CXCL12 was noted as the lesions progressed (FIG. 1, A-F and M-O). In squamous neoplastic lesions (FIG. 1, A-F) the intensity of CXCL12 was most marked in CIN3, MI and INV.SCC and in CIN3, the antigen was present throughout the full thickness of the epithelium. In CIN1 and CIN2, antigen expression was confined to the basal layers of the epithelium. Normal squamous epithelium of the ectocervix was negative. In glandular lesions, the neoplastic epithelial cells of AIS showed intense CXCL12 staining of their luminal border; whereas the neoplastic cells of ADENOCA exhibited strong positive intracytoplasmic and luminal border staining for CXCL12 (FIG. 1, N and O). Normal glandular epithelium of the endocervix was consistently negative for CXCL12 (FIG. 1M).

Example 2

Figure 2D:
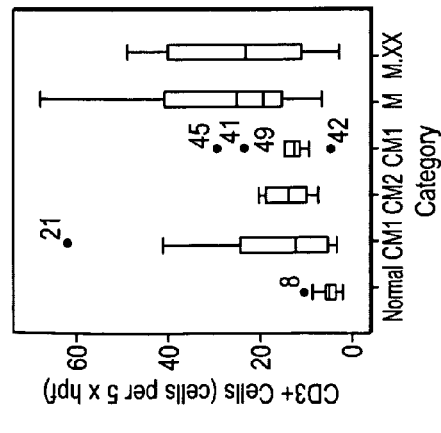
Figure 2F:
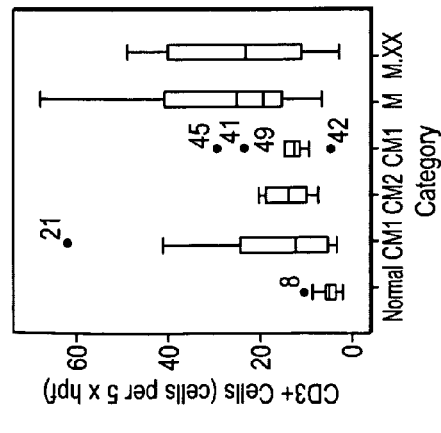
Figure 4A:
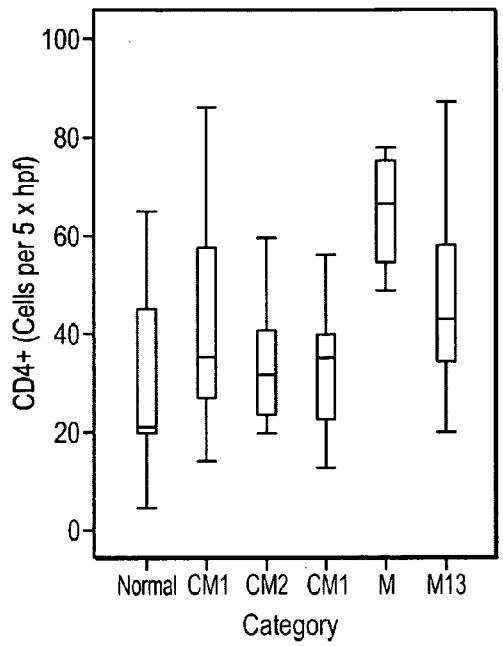
FIGS. 4A-4H are graphs showing a quantitative assessment of CD4+, CD8+ and FoxP3 positive cells in normal and dysplastic cervix. Boxplots of CD4+ (4A) or CD8+ (4B) in normal ectocervix and grades of dysplastic lesions including CIN 1, CIN2, CIN 3, MI and INV SCC. CD4 cell count increase correlates with the severity of the neoplastic lesion (ANOVA test $p<0.005$ and Linear Contrast test $p=0.01$; assuming unequal variances). Iincrease of CD8 T cell infiltrate with MI and INV.SCC (ANOVA test $p=0.005$ and Linear Contrast test $p=0.005$; assuming unequal variances). Boxplots of CD4+ (4C) or CD8+ (4D) in normal endocervix and grades of dysplastic lesions including AIS and ADENOCA. CD4 cell count increase correlates with the severity of the neoplastic lesion (ANOVA test $p<0.005$ and Linear Contrast test $p=0.01$; assuming unequal variances). Increase of CD8 T cell infiltrate with MI and INV.SCC (ANOVA test $p=0.005$ and Linear Contrast test $p=0.005$; assuming unequal variances). Boxplots of FoxP3+ cells in ectocervix and associated dysplastic lesions and endocervix and AIS/ADENOCA are shown in FIGS. 4E and 4F, respectively. An increase in FoxP3 cell count with increasing severity of the squamous neoplastic lesions is noted (ANOVA test $p<0.001$ and Linear Contrast test $p<0.001$; assuming unequal variances). An increase in FoxP3 cell count with increasing severity of the glandular neoplastic lesions is also detected. (ANOVA test $p=0.006$ and Linear Contrast test $p=0.001$; assuming unequal variances). Correlation graphs of CXCL12% Area with FoxP3+ cell counts for normal ectocervix and endocervix with neoplastic squamous (4G) and glandular lesions (4H) show highly significant correlations between the two variables measured (Pearson correlation test $p<0.001$, $r^2=0.191$ and $p<0.001$, $r^2=0.593$, respectively).
Figure 4B:
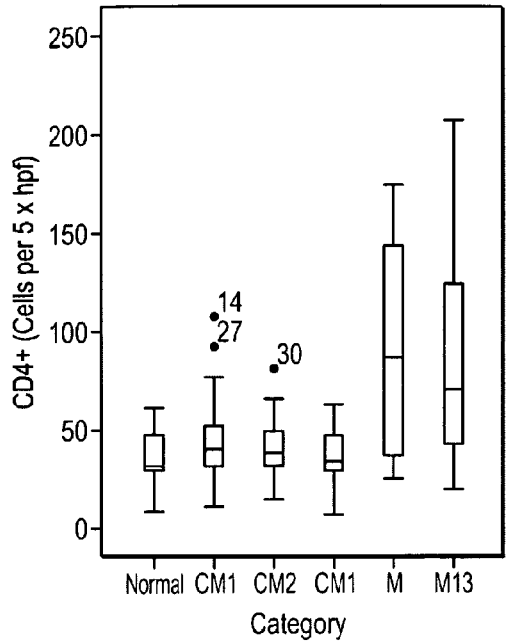
Figure 4C:
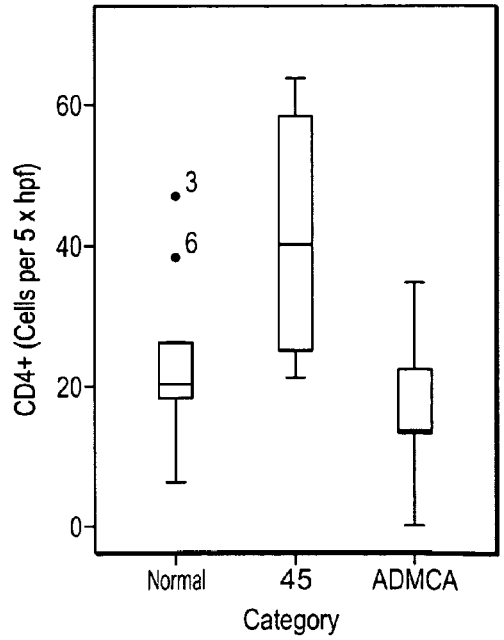
Figure 4D:
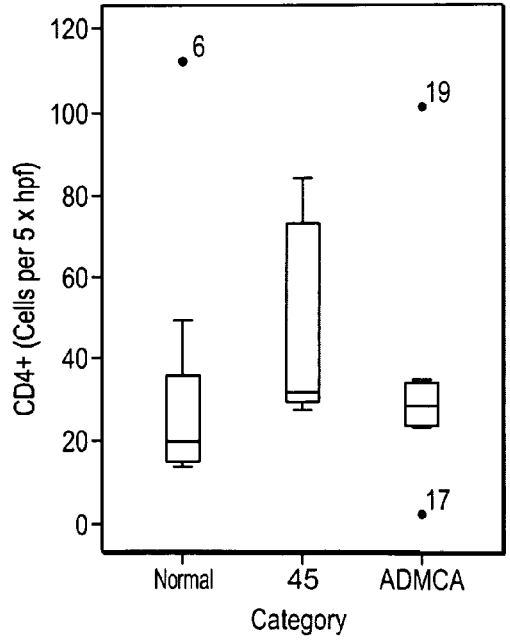
Figure 4E:
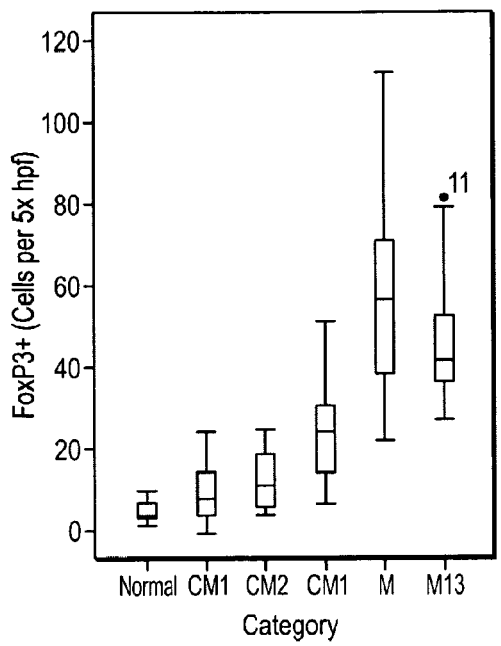
Figure 4F:
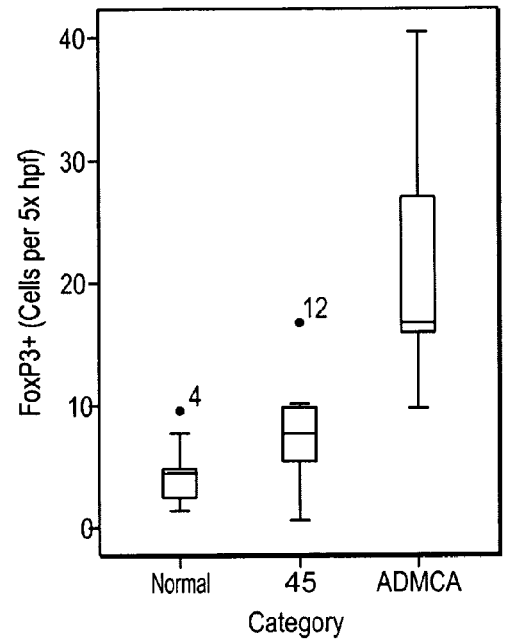
Figure 4G:
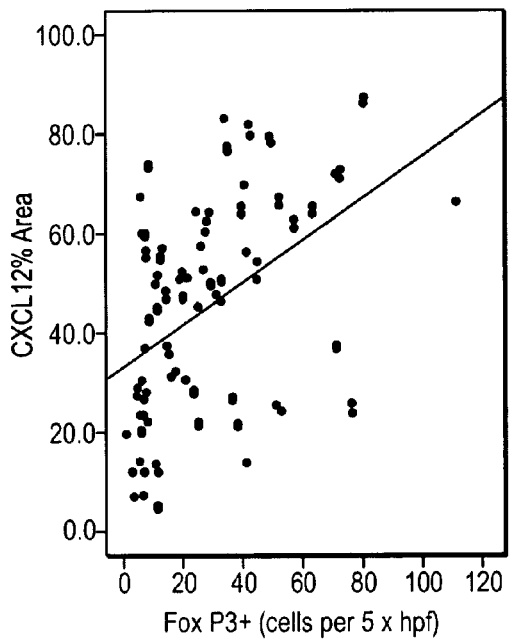
Figure 4H:
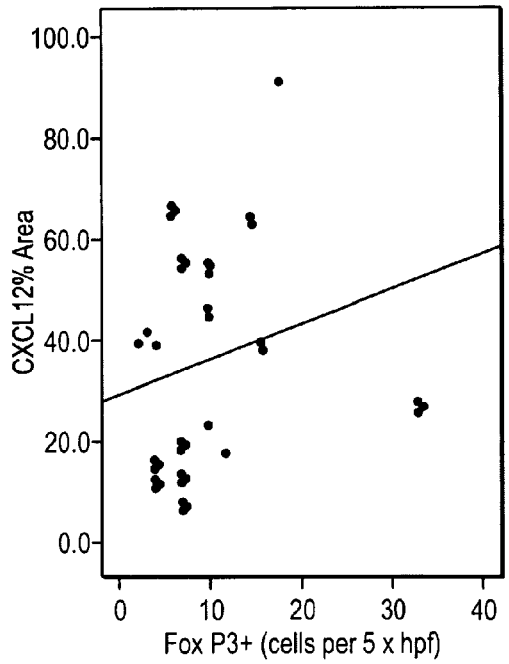

CXCL12% Area Increased with Increased Severity of Cervical Squamous and Glandular Neoplastic Lesions 383 TMA tissue cores (prepared from 83 positive cases and 24 controls) stained by the double IF staining method were analysed quantitatively for CXCL12% Area and CD3 count using the image analysis programs described above. A significant increase in CXCL12% Area with increasing severity of the cervical neoplastic lesions was observed for both squamous ($p<0.001$) and glandular neoplastic lesions ($p=0.005$) (FIG. 2, A and C). A significant increase in CD3 positive T cell counts with increasing severity of the neoplastic lesions was also seen in squamous cervical neoplasia ($p<0.001$) (FIG. 2 B) although this was not observed in glandular cervical neoplasia (FIG. 2D). A significant correlation between CXCL12% Area and CD3 cell count for was also noted for all squamous categories ($p=0.003$; $r^2$ 0.119) (FIG. 2 E), but not for the glandular lesions (FIG. 2F). The distribution and intensity of CXCL12 staining in squamous and glandular lesion as determined by the ABC(AP) staining method was almost identical with the distribution and intensity of CXCL12 demonstrated by IF staining; both showed an increase in distribution and intensity as the cervical lesions progressed through CIN1, 2 and 3 to invasive cancer and through AIS to invasive adenocarcinoma (FIG. 1).

Example 3

Infiltrating FoxP3+ T Cells Increased as Neoplastic Lesions Progressed from Preinvasive to Invasive Carcinoma In view of the above findings, subpopulations of T cells within the TMA tissue cores were examined. CD4 and CD8 antigens were observed to be membrane bound whereas the FoxP3 antigen was expressed intracellularly. Small mononuclear cells positive for these antigens were noted at all stages of development of cervical cancer and were predominantly located in the stroma (FIGS. 3A-3F). The antigen positive cells were counted using a manual counting method (positive cells were counted in 5 randomly selected fields viewed at ×400 magnification) and the mean value obtained for each category. A slight upward trend in mean CD4 and CD8 cell count ($p=0.01$ & $p=0.005$, respectively) was observed with increasing severity of the squamous neoplastic lesions (FIG. 4, A and B), but this was not present in glandular neoplastic lesions (FIG. 4, C and D). In contrast, there was a marked increase in the number of infiltrating FoxP3+ T cells as the squamous and glandular neoplastic lesions progressed from preinvasive to invasive carcinoma (p<0.001 & p=0.001, respectively) (FIG. 4, E and F). Correlation graphs of FoxP3 cell counts and CXCL12% area showed a highly significant correlation for both squamous (p<0.001; $r^2$=0.191) and glandular (p<0.001; $r^2$=0.593) categories (FIG. 4, G and H). No significant correlation was detected for CXCL12% area and CD4+ or CD8+ T-cell subpopulations (data not shown).

This example shows that CXCL12 CXCL12 expression and T cell infiltration, detected with the T cell markers CD3, CD4, CD8, and FoxP3, increased with increasing stage of squamous and glandular cervical neoplasia, as observed by immunohistochemical analysis of these tissues. The results in this example indicate that CXCL12 and FoxP3 are useful biomarkers for staging cervical cancer in tissue samples.

Example 4

Figure 5A:
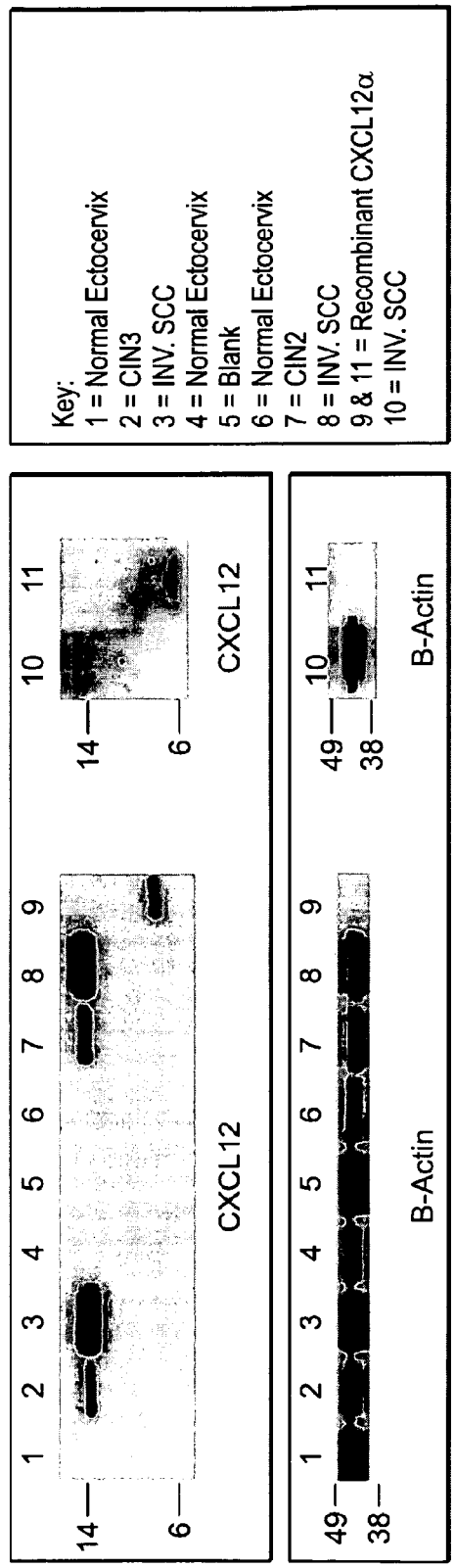
FIGS. 5A and 5E show an analysis of CXCL12 in neoplastic and normal cervical tissue.
Figure 5B:
FIG. 5B shows representative examples of in situ hybridization of TMA sections using two Bond probes (HPV 6,11 and HPV 16+). CIN1 showing positive nuclear staining (brown) for HPV 6.11.
Figure 5C:
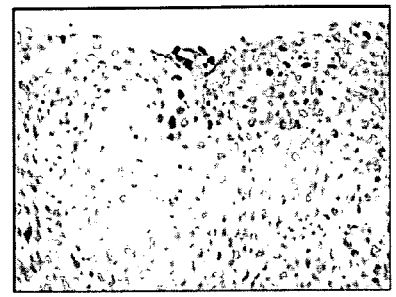
FIG. 5C provides a CIN3 sample showing positive nuclear staining for HPV 16+.
Figure 5D:
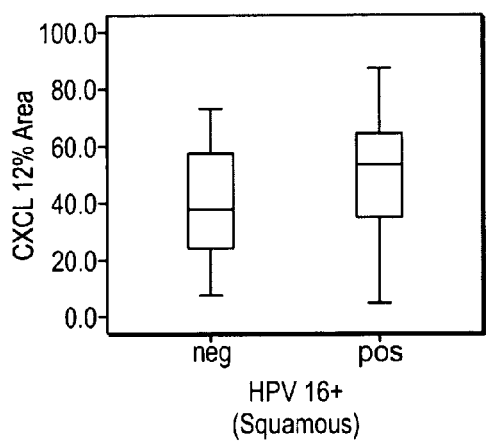
FIG. 5D is a boxplots of CXCL12% Area of HPV 16+ probe negative (neg) and HPV16+ probe positive (pos) cases for pooled samples of normal ectocervical and squamous neoplastic lesions are shown. Independent sample T-test shows a significant difference between the two groups ($p<0.05$, assuming equal variances).
Figure 5E:
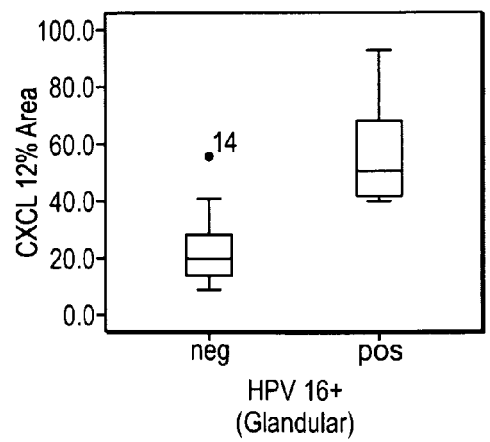

CXCL12 was Expressed at Higher Levels in Invasive Cervical Carcinoma than in Normal Tissues In order to confirm the expression of CXCL12 by tissues examined in this study both Western Blots and ELISAs were performed on tissues. An increasing percentage of cases showed a positive CXCL12 alpha band in the 14 kDa molecular weight range with progression of cervical neoplasia. All normal cervical tissue samples were negative. As shown by the representative blot in FIG. 5A, CXCL12 was absent in normal ectocervical tissue (lanes 1 and 4) and normal endocervical tissue (lane 6), but was present in samples from preinvasive and invasive cervical carcinoma (CIN2, CIN3 and INV.SCC). In one sample of INV.SCC (lane 5) a band corresponding to CXCL12 was not detected. However a repeat sample from the same specimen showed a positive band (lane 10). In general, samples of INV.SCC had stronger bands of CXCL12 expression (lanes 3 and 8) than samples of preinvasive cervical neoplasia samples (lanes 2 and 7). ELISA showed that the amount of CXCL12 in INV.SCC was 3-4 times greater than the amount in normal cervix. The mean value for CXCL12 for normal cervix (5 cases)=57.6 (+/−9.4) ng/ml (range 28.5-85.6 ng/ml) and the mean value for CXCL12 for INV.SCC (5 cases)=232+/−51.4 ng/ml (range 114-356 ng/ml) (p=0.0018, Student's T test). CXCL12 was detectable by ELISA and on Western from dysplastic cervical lesions and the chemokine was expressed at significantly higher levels in INV.SCC than in normal cervix. The results in this example indicate that SDF-1 is a useful biomarker for staging cervical cancer in tissue samples.

Example 5

Increased CXCL12 Staining was Identified in HPV Positive Samples Relative to HPV Negative Samples Positive nuclear staining was seen mainly in the surface layers of the squamous epithelium (FIG. 5, B and C) and characteristically associated with koilocytosis. HPV typing was performed on tissue samples (TMA) from 81 cases where there was an adequate amount of tissue as described above. The prevalence of HPV antigen in the squamous and glandular lesions was as follows: thirty one (38%) and 52 (64%) of the 81 TMA sections were positive for HPV6,11 and HPV16+ probes respectively. Fourteen percent (14%) of normal cases were positive for HPV16+ compared with 75% of the neoplastic cases. Table 2 (below) reports HPV typing against histopathological staging of cervical cancer, CXCL12% Area and FoxP3 cell count.

TABLE 2

| Group Number HPV Probes | Normal Endocx (n = 6) | CIN1 (n = 10) | CIN2/3* (n = 33) | INV SCC (n = 14) | Normal Endocx (n = 9) | AIS (n = 5) | ADENOCA (n = 5) | CXCL12% Area Mean ± SD | FoxP3 Cell Count Mean ± SD |
|---|---|---|---|---|---|---|---|---|---|
| Group 1 6, 11 Negative 16+ Negative | 3 | 4 | 3 | 2 | 4 | 2 | 1 | 30.63 ± 19.22 (n = 26) | 13.2 ± 22.4 (n = 20) |
| Group 2 6, 11 Positive 16+ Negative | 0 | 0 | 2 | 1 | 0 | 0 | 0 | 52.14 ± 9.33 (n = 3) | 46 ± 5.7 (n = 2) |
| Group 3 6, 11 Negative 16+ Positive | 1 | 4 | 7 | 5 | 2 | 3 | 3 | 35.98 ± 7.30 (n = 24) | 20 ± 13.7 (n = 22) |
| Group 4 6, 11 Positive 16+ Positive | 0 | 3 | 10 | 3 | 0 | 0 | 1 | 6075 ± 1064 (n = 20) | 28.9 ± 20.6 (n = 20) |

*includes MI

Table 2 shows HPV typing, CXCL12% Area and FoxP3 cell count in low and high risk HPV-typing study groups. These data show an increasing percentage of high risk HPV 16+ positive cases as the neoplastic lesions progress: Normal Ectocx=17%, CIN1=60%, CIN2/3=79%, INV.SCC=79%, Normal Endocx=13%, AIS=60%, ADENOCA=80%. Table 2 also shows (AIS) or invasive adenocarcinoma (ADENOCA). FIG. 5 shows HPV status vs the CXCL12% area and Fox p3 cell counts for pooled squamous and glandular neoplastic lesions (including normal ecto and endocervix). A significant increase in CXCL12% area between HPV-negative lesions (Group 1) and other HPV positive groups was detected (Group 2; p=0.0099; Group 3, p=p=0.0321 and Group 4 p<0.0001)(unpaired two sample t-test with unequal variances and unequal sample size). A significant difference in CXCL12% area was also detected between HPV-positive lesions in Groups 2 and 3 (p=0.0002). Study of HPV status versus FoxP3-positive cell count revealed an increased presence of FoxP3 positive cells in Groups 2, 3 and 4 containing HPV positive lesions compared to Group 1 containing HPV negative lesions. These differences did not reach statistical significance (Group 1 versus Group 2; p=0.0757; versus Group 3, p=0.7441 and Group 4, p 0.0885).

Progression of neoplastic lesions was associated with an increasing percentage of HPV16+ positive cases (Normal Ectocx=17%, CIN1=60%, CIN2/3=79%, INV.SCC=79%, Normal Endocx=13%, AIS=60%, ADENOCA=80%). CXCL12% Area was significantly increased in cases that were positive for both HPV 6, 11 and HPV 16+ probes compared to cases that were negative for both probes (p<0.0001). Furthermore, cases that were positive for only HPV 6, 11 demonstrated a higher CXCL12% Area than those that were HPV 16+ positive alone (p=0.0002). A higher number of FoxP3 positive cells was detected in cases that were positive for both HPV 6,11 and HPV 16+ (18.2 vs 28.9) and in cases that were positive only for HPV 6,11 in comparison to HPV-negative samples, but these associations did not reach statistical significance possibly because of low sample number (18.2 vs 48, p=0.0885 and 0.0757, respectively). Comparison of CXCL12% Area in HPV16+ probe positive and HPV16+ probe negative cases showed a significant difference between the two groups for both pooled samples of normal ectocervix and squamous neoplastic lesions (p=0.05) and pooled samples of normal endocervix and glandular neoplastic lesions (p=0.001) (FIG. 5, D and E). Significantly higher levels of CXCL12 staining were seen in all HPV positive samples compared to all HPV negative samples in this context (p<0.0001).

Example 6

Robust Differences is CXCL12 Staining were Found Between Dyskaryotic Vs Normal Epithelial Cells in Thin Prep Cytological Specimens Prepared from Cervical Scrapes Thin Prep™ Smears were screened for CXCL12 localisation as evidenced by brown staining of the cytoplasm of the epithelial cells. Intense brown staining was noted in the cytoplasm of dyskaryotic cells in the 7 specimens known to be positive for malignancy (FIG. 6, C-E), whereas no staining was seen in the normal mature squames or endocervical cell clusters in either the 5 negative or 7 positive cases (FIG. 6, A and B). Faint brown staining of very occasional discrete immature metaplastic cells was observed in 3 specimens, but the benign nature of the cells was obvious from their morphology. The distinction between dense CXCL12 staining in dyskaryotic cells from positive cases versus faint or absent staining in normal epithelial or metaplastic cells was robust for all samples in this study.

This study has shown that there was a significant increase in the expression of the chemokine CXCL12 as measured by IHC and ELISA in cervical epithelium as the neoplastic lesions progressed from preinvasive to invasive cancer. This study also showed that CXCL12+ was not expressed by normal cervical squamous or glandular epithelium. The difference in the intensity of staining between the normal cervical epithelium and low and high grade precancerous lesions and invasive cancer was verified by Western blot. These findings complement studies that investigated expression of CXCR4 in tissue sections from patients with clinically invasive cervical cancer with respect to the potential for metastatic spread of tumour (Majka et al., Folia Histochem Cytobiol 2006, 44(3):155-64 20, 21, Zhang et al., Int J Gynecol Cancer 2007, 17(2):478-83, Yang et al., Int J Gynecol Cancer 2007, 17(3): 676-86).

The focus of the present study is the role that CXCL12 plays in dysregulating T cell infiltration into cervical cancer as it progresses from preinvasive to invasive disease. CXCL12 has the potential to modulate efficacious antitumor responses in view of its properties as a powerful chemoattractant for T and pre-B lymphocytes and dendritic cells to the tumor site (Zou et al., Nat. Med. 2001, 7:1339-1346). However, the antitumor activity of CXCL12 is tightly regulated by local levels of CXCL12. Dunussi-Joannopoulos provided experimental evidence that low levels of CXCL12 are associated with antitumor response whereas high levels may inhibit T cell attraction (Zou et al., Nat. Med. 2001, 7:1339-1346). The present study showed that tumor progression as measured by clinicopathological stage of cervical neoplasia, was associated with $CD3^+$ T cell infiltration into the tumor. Furthermore, the most significant association was between advanced stage of tumor progression and high levels of $FoxP3^+$ T cells in the tumor. Of particular significance was the correlation between CXCL12 expression and FoxP3 for both squamous and glandular cervical neoplastic lesions. These results indicate that high levels of CXCL12 lead to retention or accumulation of $FoxP3^+$ T cells in the progressing cervical cancer. A weak correlation was demonstrated between $CD4^+$ and $CD8^+$ T cell infiltration and tumor progression, and no correlation was reported between CXCL12% Area and other T cell subpopulations, thus reinforcing the role of FoxP3+ T-cells in this context and confirming a previously reported not clear relationship between the T cell infiltration and tumor progression (Clark et al., Mod Pathol 2009; 22(3):393-402).

The role of the axis CXCL12/CXCR4 in tumor spread and progression has been demonstrated in various cancer models. CXCR4 is the most constantly expressed receptor in cancer (Balkwill, Semin Cancer Biol 2004, 14(3):171-9), and its level in tumor tissue has been correlated with clinical outcomes (De Falco et al., Cancer Res 2007, 67(24):11821-9 27, Kajiyama et al., Int J Cancer 2008, 122(1):91-9). In addition, CXCL12 expression has been directly correlated with known determinants of immune dysregulation, such as HPV infection itself (Sheu et al., J Obstet Gynaecol Res 2007, 33(2): 103-13) and T-regs infiltration (Curiel et al., Nat Med 2004, 10(9):942-9, Perrone et al., Eur J Cancer 2008, 44(13):1875-82). A direct relationship between the HPV infection and the onset of an immune suppressive environment has been suggested by a prospective study of HPV-16 related lesions, in which T-regs frequencies were significantly increased in women who had persistent HPV16 infection and HPV16 specific IL-2 producing T-helper cells (Molling et al., Int J Cancer 2007, 121(8):1749-55). Furthermore, it has also been observed that, in patients with HPV6 and HPV11-derived genital condylomata, FoxP3+ regulatory T cells with a suppressive cytokine milieu accumulated in large warts (Cao et al., J Immunol 2008, 180(11):7681-6). The WHIM syndrome, which is a syndrome characterized by disseminated HPV-induced warts, leukopenia due to bone marrow cell retention and other immune dysfunctions, has been correlated to a defect in CXCR4 receptor and CXCL12 signal transmission, thus confirming a major role of the cytokine in contributing to immune cell dysregulation and T cell impaired trafficking in the context of HPV-derived lesion (Balabanian et al., J Clin Invest 2008, 118(3):1074-84)s.

The results reported herein identify a significant relationship between HPV typing and CXCL12% Area in both squamous and glandular neoplastic lesions, showing an increase of CXCL12% Area in cases that were positive for both HPV 6, 11 and HPV 16+ probes compared to cases that were negative for both probes. Interestingly, cases that were positive for only HPV 6, 11 demonstrated a higher CXCL12% Area than those that were only HPV 16+ positive. Despite the higher values reported between HPV status and FoxP3-positive cell count in cases that were positive for both HPV 6,11 and HPV 16+ and in cases that were positive only for HPV 6,11, the results did not reach significance because of a low numbers of samples in certain groups due to a lack of available tissue.

In this study, the link between HPV, CXCL12, FoxP3+ T infiltrating cells, and tumor progression has been shown through multiple assays, histopathologically and immunologically, and proven both in squamous and glandular neoplastic cervical lesions. Thus, CXCL12 is a good candidate as a marker of cervical cancer clinical progression through the well established multi-step histological patterns of preinvasive, microinvasive and invasive cancer.

Several large studies have shown that virtually all squamous cell carcinomas of the cervix and most of the adenocarcinomas are HPV-positive and these results are consistent with these findings. Over 80% of the preinvasive and invasive lesions tested were positive for the most common high risk HPV. Integration of viral DNA into the host genome is an essential step in the carcinogenic process and although integration can occur at a number of sites in the viral genome, integration in the region of the E2 gene causes loss of transcriptional control of E6 E7 with subsequent loss of function of the p53 and the Rb pathways resulting in uncontrolled cell proliferation (Tjalma et al., Best Pract Res Clin Obstet Gynaecol 2005, 19(4):469-83).

Example 7

CXCL12 is a Biomarker for Ovarian Cancer

Figure 7A:
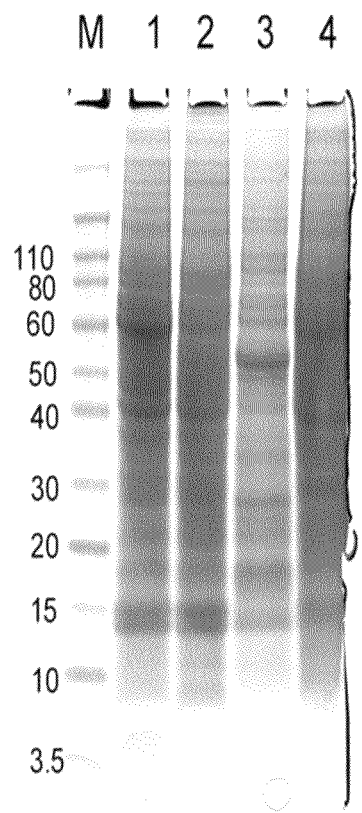
FIGS. 7A and 7B show an SDS-PAGE used to separate ovarian cancer cell lysates and a corresponding Western blot. When probed with anti-CXCL12, 8 and 14 kD CXCL12 polypeptide isoforms were detected.

Four ovarian tumor cell lines were obtained. These ovarian cancer cells were described by Xing and Orsulic in Cancer Research 66, 8949-8953, Sep. 15, 2006. Tumours were extracted with RIPA buffer in the presence of protease inhibitors. Supernatants were collected and protein concentration was determined 60 micrograms of protein per lane was separated on an SDS-PAGE gel. One gel was transferred to Nitrocellulose the other was stained with Rapid Stain (FIG. 7A).

Figure 7B:
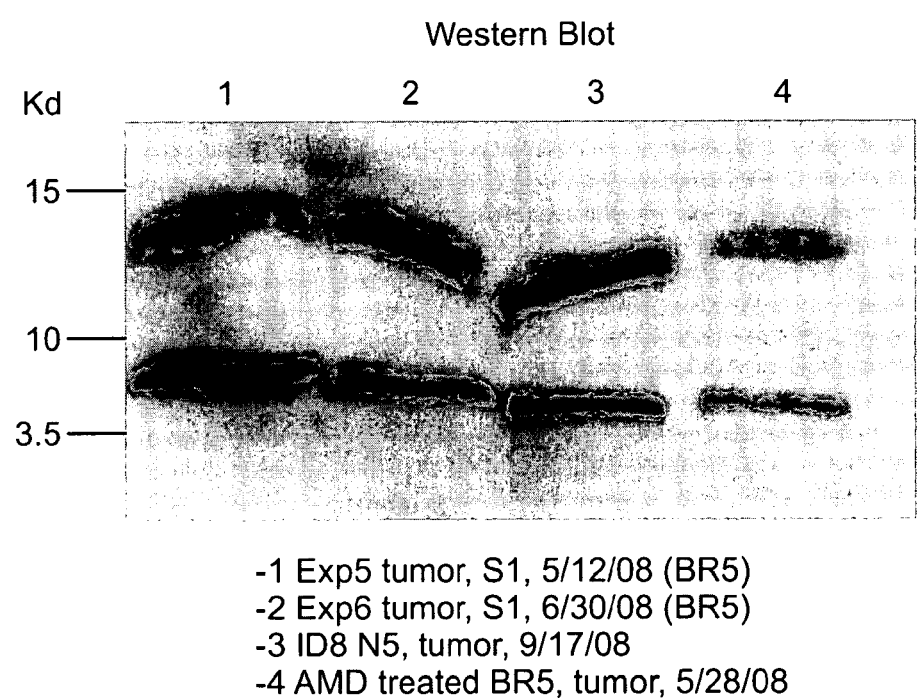

For Western blot analysis the membrane was blocked with milk, 1% horse serum and 1% normal goat serum. The membrane was probed with biotinylated Goat anti-SDF-1 (R&D Systems cat# BAF310; 0.2 µg/ml in block buffer), then washed with PBS Tween 20 (0.05%). Binding was detected with Streptavidin HRP (10000 fold diluted in block buffer) using West Pico substrate (Pierce). The Western blot indicated that a 13-14 kD CXCL12 isoform polypeptide, as well as an 8 kD CXCL12 isoform was expressed by ovarian cancer cells (FIG. 7B).

The results described above were carried out using the following methods and materials.

Selection of Cases for Tissue MicroArray (TMA)

Cases with a diagnosis of preinvasive, microinvasive, or invasive squamous cervical cancer and cases with preinvasive or invasive adenocarcinoma were selected from the Hammersmith Hospital's computerised patient records. The corresponding Haematoxylin and Eosin (H&E) stained histological slides were retrieved from the hospital file and reviewed by a consultant pathologist. On the basis of microscopic review, the slides were then assigned to one of seven categories each reflecting a histopathologically defined stage in the development of cervical cancer i.e CIN1 (with or without HPV changes), CIN2, CIN3, microinvasive squamous carcinoma (MI), invasive squamous cell carcinoma (INV.SCC), adenocarcinoma in situ (AIS) or invasive adenocarcinoma (ADENOCA). The paraffin-embedded formalin fixed tissue blocks were then retrieved from the Histopathology archive together with control blocks containing normal ectocervical or endocervical tissue. A total of 107 cases were identified as suitable for TMA. These included 83 positive cases comprising CIN1+/− HPV (n=15), CIN2 (n=15), CIN3 (n=20), MI (n=7), INV.SCC (n=15), AIS (n=6), ADENOCA (n=5); and 24 control cases, i.e normal ectocervix/squamous epithelium (9) and endocervix/glandular epithelium (n=15). Three hundred and forty eight (348) tissue cores were prepared from the 83 positive cases by TMA comprising CIN1+/− HPV (n=30), CIN2 (n=43), CIN3 (n=99), MI (n=27), INV.SCC (n=116), AIS (n=12) and ADENOCA (n=21). In addition, 14 cores from normal ectocervix and 21 cores from normal endocervix were prepared by TMA. This study was performed with ethical approval from the Hammersmith and Queen Charlotte's & Chelsea Research Ethics Committee REC (reference 05/Q0406/170).

Manual Tissue Microarray (TMA)

A manual tissue microarrayer [Beecher Instruments Inc. Sun Prairie, Wis. 53590] was used to prepare sections for histological & immunohistochemical staining and in situ hybridisation. For this study, 7 blocks were prepared (labelled B to H) and from 50 to 100 tissue cores arrayed in each block. Representative areas were first selected from each donor tumor block by pre-marking sampling regions from the corresponding H&E stained histological slide. The pre-marked H&E slide and the corresponding tissue block were then aligned and the slide moved out so that tissue cores of about 1.0 mm in diameter could be punched using the arraying device and then arrayed into a recipient block. Serial 2 µm sections of the resultant TMA blocks were cut using a rotary microtome [AS 325, Shandon, UK]. The blade was wiped with 70% ethanol to avoid cross-contamination. For every fifth level, a section was stained with H&E stain and kept for comparison with the IHC sections.

Immunohistochemical (IHC) Staining Methods

Two methods of IHC staining were used for this study—the avidin-labelled biotin complex (ABC) IHC staining method and a double immunofluorescence (IF) staining method. The ABC method was used to investigate the distribution of a single specific antigen in each section, e.g. CXCL12 (R and D, USA) or T cell marker (CD3, CD4, CD8, FoxP3) [Novocastra and E-bioscience, UK]; the IF method was used to study the distribution of both CXCL12 and CD3 antigens in the same section. In (ABC) IHC staining, after dewaxing and rehydration of sections, antigen retrieval was performed using the microwave method in 0.01 M buffered sodium citrate solution (pH 6.0). After inactivation of endogenous peroxidase with 0.3% hydrogen peroxide in methanol (for peroxidase detection method only) and blocking non-specific background staining with normal goat serum, sections were then incubated with the primary antibody. After an overnight incubation, sections were then incubated with the appropriate biotinylated secondary antibody followed by a peroxidase- or alkaline phosphatase-labelled avidin biotin complex [Vectorlab, UK]. The enzyme signal was detected with Diaminobenzidine/$H_2O_2$ (DAB) for Peroxidase, Px [Vectorlab, UK] or Fast Red with Naphthol Phosphate Substrate for Alkaline Phosphatase, AP [Biogenex, UK]. Harris hematoxylin was used as a counterstain for Px sections whereas Mayer's haemalum was used for AP sections. Sections were mounted using DPX (Px) or aqueous mountant (AP) for examination in the light microscope. In double IF staining, sections were pre-treated as described for the IHC method, and then incubated with a mixture of the two primary antibodies followed by application of a mixture of two suitable secondary antibodies with different fluorescent labels ie CY3 and Alexa Fluor. After incubation in the dark with double fluorescence-linked secondary antibodies, sections were mounted with Slowfade® Gold antifade reagent with DAPI [Invitrogen, UK]. PBS was used in place of the primary antibody as a negative antibody control. Thymus sections were used as positive tissue controls. Stained slides were then viewed using the Nikon Eclipse 80i/Olympus BX40 Fluorescence Microscope. Red coloured images of CXCL12 expression and green coloured images of CD3 T cells were visualised using green and blue filters, respectively and assessed manually in the first instance. Nuclear staining (blue) was performed with Meyer's haemalum for the (ABC) IHC staining method and with DAPI (4'-6-Diamidino-2-phenylindole) for the double IF staining method. Thereafter they were analysed quantitatively using the Image PRO® Plus [6.0 Version].

Imaging and Quantitation of IF TMA Sections Using Image PRO® Plus (6.0 Version)

All images of IF and H&E stained sections were taken using a digital camera [Nikon DXM 1200F, Nikon, UK] and then saved as JPEG or TIFF. From the IF stained sections, an average of 5 images per TMA core were taken at ×400 magnification. Each image had approximately the same area of squamous or glandular epithelium together with stroma directly underneath it. Expression of CXCL12 antigens and CD3+ T cell count were analysed using the image analysis programme Image PRO® Plus 6.0. Two parameters were chosen to quantify CXCL12 expression from the IF stained tissue sections, namely CXCL12 intensity, and CXCL12 percentage Area. Both parameters were evaluated using a prerecorded "Macro" containing a set of commands that had been designed by the user (FJ) to allow repeated performance of a certain set of measurement on the image to be analysed. For this study, a set of commands called Macro 1 were designed for the purpose of evaluating the intensity and % Area for each fluorescent colour channel ie CY3-Red (550 nm), Alexa Fluor-Green (488 nm) and DAPI-Blue (365 nm). The CD3+ T cells which were conjugated to the Alexa Fluor® fluorochrome were identified on the images after eliminating the other two fluorescent colour channels (red and blue) and counted manually at ×400 magnification in 5 randomly selected fields per tissue core. The CD3 positive cell counts were recorded on Image PRO® Plus. The data obtained from Image PRO® Plus were used to provide the mean values of intensity and percentage Area of CXCL12 as well as the mean values of CD3 T cell count. The mean value assigned to each tissue core was obtained from the mean values of all the images analysed for the tissue core. The results of digital evaluation of CXCL12 in the IF stained sections were subsequently compared for intensity and localisation of CXCL12 in ABC stained sections.

Western Blotting and ELISA Measurement of Tissue CXCL12 Concentrations

Protein lysates were extracted from fresh snap frozen human cervical tissues which had been obtained directly from colposcopic biopsies or the tissue bank at the Hammersmith Hospital: normal cervix (n=9), CIN1 (n=3), CIN2-3 (n=15); INV.SCC (n=6). A frozen section was prepared from each sample and stained using hematoxylin and eosin to ascertain the presence of normal or abnormal cervical epithelium prior to tissue lysis. In some of the samples were seen to contain a small amount of stroma was observed beneath the epithelial layer.

Human recombinant CXCL12 [Peprotech, UK] was also run at 100 ng/lane for every blot to serve as a positive control. Protein assay of these lysates was then performed using Bio-Rad protein assay kit. Proteins were separated in 12% SDS-PAGE [Novex Mini Gel, Invitrogen, UK], transferred onto a nitrocellulose membrane and stained overnight with anti-SDF-1 antibody (R&D Systems, USA), followed by detection using horseradish peroxidase (HRP)-labelled antimouse antibody [Santa Cruz, USA] and an enhanced chlorouluminescence (ECL) kit [Amersham Biosciences, Piscataway, N.J.]. The quantity of human CXCL12 present in tissue homogenates prepared from snap frozen tissue obtained from the same source as above was determined by specific ELISA Quantikine® human CXCL12 Immunoassay [R&D systems, Minneapolis, Minn.]. The specimens selected for ELISA assay comprised normal thymus (n=1) normal cervix (n=5) and INV.SCC (n=5). Each tissue sample (100 mg) was cut into small pieces using forceps, scissors and a disposable scalpel and put in a cryotube of 1.8 ml adding 1-1.5 ml of DMEM. The tissue pounded inside the cryotube was cut down using a disposable scalpel and the tubes vortexed to mix thoroughly. Cells were lysed by the freeze-thaw method (thaw at 37° C. and immediately return to −80° C. for three cycles), transferred into 3 ml syringe fitted with 0.22 µm filter [Millex Ha 0.45 microm filter unit, Millipore Corporation, Carrightwohill, Cork, Ireland] and pushed through the filter to remove large pieces of cell debris. Extracts were analyzed using the human CXCL12 Quantikine ELISA kit and the absorbance of each well determined using a microplate reader at 450 nm [Tecan Spectra Fluor microplate reader, UK]. The absolute CXCL12 concentration was determined using a standard curve for CXCL12 according to the manufacturer's recommendations.

HPV In-situ Hybridisation (ISH)

TMA tissue sections from 81 of the original 107 cases (Table 2) were used for this study. The cases included CIN1 (n=10), CIN2 (n=10), CIN3 (n=18), MI (n=5), INV.SCC (n=6), AIS (n=5), ADENOCA (n=5), normal ectocervix (n=6) and normal endocervix (n=8). HPV DNA was detected using the Bond™ System [Leica Microsystems, UK], a fully automated system for ISH staining Two biotin-conjugated DNA probes [Vision BioSystems, UK] were used in the Bond system for ISH: one probe (designated HPV 6, 11) detected the low-risk HPV types 6 and 11; and the other probe (designated HPV 16+) detected the high-risk HPV types 16, 18, 31, 33, 51. Both DNA Negative and DNA Positive Controls were processed at the same time as the cases. The protocol for HPV DNA ISH process using Bond™ polymer refine detection kit [Leica Microsystems Bond™ system] was followed according to the manufacturer's instructions. Control slides were checked under the microscope before the sections were dehydrated for permanent mounting. Positive cases were identified by the presence of dark brown DAB stained nuclei. The HPV status of the TMA sections was correlated with the CXCL12% Area on the serial sections from the same specimen as determined by IHC and Image PRO as described earlier.

Staining of Thin Prep Cervical Smears for CXCL12 Expression

Slides from 12 cervical scrape liquid based cytology (LBC) specimens which had previously been reported as containing severely dyskaryotic cells (7 specimens) or reported as negative for malignancy (5 specimens) were prepared by the Thin Prep™ method and fixed in alcohol. Slides were immersed in 0.01 M buffered sodium citrate solution (pH 6.0) and microwaved for antigen retrieval. Endogenous peroxidase was inactivated with 0.3% hydrogen peroxide in methanol and non specific background staining blocked by treatment with normal goat serum. Slides were then incubated with anti-human CXCL12 antibody [clone 79018: 1 in 100, R&D, USA]. PBS replaced the primary antibody as negative control. The second incubation was in biotinylated goat antimouse Ig [Vectorlabs, UK] followed by a peroxidase-labelled avidin/biotin complex. Diaminobenzidine/$H_2O_2$ (DAB) was used for signal detection with Harris Haematoxylin as nuclear counterstain. Slides were mounted in DPX.

Statistical Analysis

Specimens were categorised according to histological status (normal ectocervix, CIN1, 2 &3, MI and INV.SCC and normal endocervix, AIS and ADENOCA) and mean values for CXCL12% Area and T cell counts were determined for each category. Differences between categories were examined using ANOVA after testing for normal distribution and values were used where appropriate (namely, CD4, CD8 and FoxP3). A linear contrast test was used to determine if there was a trend for increasing severity across the categories, taking into account unequal variance. Linear regression was used to examine the correlation between the variables CXCL12% Area and FoxP3 T cell count. A significance level of 5% was used in all the tests. Statistical analysis was performed using SPSS software version 15.0.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for staging cervical neoplasia in a subject and administering a treatment correlated to a good clinical outcome for the stage of cervical neoplasia, the method comprising:
   A) performing an assay to measure the level of a CXCL 12 polypeptide having a molecular weight greater than about 10 kD or 11 kD in the cervical neoplasia;
   B) comparing the level of the CXCL 12 polypeptide in the cervical neoplasia to a reference level;
   C) classifying the stage of the cervical neoplasia in the subject as a pre-invasive stage or an invasive stage of cervical neoplasia based on the comparison to the reference level wherein an increase in the level of the CXCL12 polypeptide relative to the reference level indicates an invasive stage and a lack of an increase in the level of the CXCL12 polypeptide relative to the reference level indicates a pre-invasive stage; and
   D) administering a less aggressive treatment to the subject having a pre-invasive stage of cervical neoplasia, or a more aggressive treatment to the subject having an invasive stage of cervical neoplasia
thereby staging cervical neoplasia in the subject and administering a treatment correlated to a good clinical outcome for the stage of cervical neoplasia.

2. The method of claim 1, wherein CXCL12 molecular weight is determined in an immunoassay, in an SDS-PAGE assay, by mass spectroscopy, by Western blot, or ELISA.

3. The method of claim 1, wherein the CXCL 12 polypeptide selectively binds a CXCL12-specific antibody.

4. The method of claim 1, wherein the CXCL12 polypeptide has at least about 85% identity to the amino acid sequence of any of SEQ ID NOs 2-7.

5. A method for treating cervical neoplasia in a subject, the method comprising:
   performing an assay to measure the level of a CXCL 12 polypeptide having a molecular weight greater than about 10 kD or 11 kD in a sample comprising cells from a cervical neoplasia;
   comparing the level of the CXCL12 polypeptide in the sample to a first and second reference level;
   administering a less aggressive treatment to the subject identified as having a level in the sample above the first reference level and below the second reference level, a pre-invasive cervical neoplasia, or administering a more aggressive treatment to the subject identified as having a level in the sample above both the first and second reference levels, an invasive stage of cervical neoplasia, thereby treating cervical neoplasia in the subject.

6. The method of claim 5, wherein the first reference level is an increase of less than about 3 fold compared to a control sample.

7. The method of claim 5, wherein the second reference level is an increase of higher than 3-fold compared to a control sample.

* * * * *